US008426374B1

(12) United States Patent
Magee et al.

(10) Patent No.: US 8,426,374 B1
(45) Date of Patent: Apr. 23, 2013

(54) METHOD FOR MODIFYING MYOSTATIN EXPRESSION

(75) Inventors: Thomas R. Magee, Cypress, CA (US); Nestor F. Gonzalez-Cadavid, Pasadena, CA (US); Monica G. Ferrini, Redondo Beach, CA (US); Jacob Rajfer, Rolling Hills Estate, CA (US)

(73) Assignee: Los Angeles Biomedical Research Institute at Harbor-UCLA Medical Center, Torrance, CA (US)

(*) Notice: Subject to any disclaimer, the term of this patent is extended or adjusted under 35 U.S.C. 154(b) by 1401 days.

(21) Appl. No.: 11/744,158

(22) Filed: May 3, 2007

Related U.S. Application Data

(60) Provisional application No. 60/798,063, filed on May 4, 2006.

(51) Int. Cl.
*A61K 48/00* (2006.01)

(52) U.S. Cl.
USPC ......... 514/44; 536/24.5; 536/24.31; 536/24.1

(58) Field of Classification Search ........................ None
See application file for complete search history.

(56) References Cited

U.S. PATENT DOCUMENTS

| | | | | |
|---|---|---|---|---|
| 6,399,312 | B2 | 6/2002 | Wu-Wong et al. | |
| 6,617,440 | B1 | 9/2003 | Findly | |
| 8,242,090 | B2 * | 8/2012 | Khachigian | 514/44 A |
| 2005/0124566 | A1 * | 6/2005 | Robin et al. | 514/44 |

OTHER PUBLICATIONS

Acosta, J., et al., "Myostatin gene silenced by RNAi show a zebrafish giant phenotype," J Biotechnol, Oct. 10, 2005, vol. 119(4), pp. 324-331.
Amali, A.A., et al., "Up-regulation of muscle-specific transcription factors during embryonic somitogenesis of zebrafish (*Danio rerio*) by knock-down of myostatin-1," Dev Dyn, Apr. 2004, vol. 229(4), pp. 847-856.
Artaza, J.N., et al., "Myostatin Inhibits Myogenesis and Promotes Adipogenesis in C3H 10T(1/2) Mesenchymal Multipotent Cells," Endocrinology, Aug. 2005, vol. 146(8), pp. 3547-3557.
Bogdanovich, S., et al., "Functional improvement of dystrophic muscle by myostatin blockade," Nature, Nov. 28, 2002, vol. 420(6914), pp. 418-421.
Bogdanovich, S., et al., "Myostatin propeptide-mediated amelioration of dystrophic pathophysiology," FASEB J, Apr. 2005, vol. 19, pp. 543-549.
Brummelkamp, T.R., et al., "A System for Stable Expression of Short Interfering RNAs in Mammalian Cells," Science, Apr. 19, 2002, vol. 296, pp. 550-553.
Cappelletti, M., et al., "Gene electro-transfer improves transduction by modifying the fate of intramuscular DNA," J Gene Med, Apr. 2003, vol. 5(4), pp. 324-332.
Elbashir, S.M., et al., "Duplexes of 21-nucleotide RNAs mediate RNA interference in cultured mammalian cells," Nature, May 24, 2001, vol. 411(6836), pp. 494-498.
Faurie, C., et al., "Cell and animal imaging of electrically mediated gene transfer," DNA Cell Biol, Dec. 2003, vol. 22(12), pp. 777-783.
Ferrini, M.G., et al., "Antifibrotic role of inducible nitric oxide synthase," Nitric Oxide, May 2002, vol. 6(3), pp. 283-294, Abstract.
Frimel, T.N., et al., "A model of muscle atrophy using cast immobilization in mice," Muscle Nerve, Nov. 2005, vol. 32(5), pp. 672-674.
Golzio, M., et al., "Inhibition of gene expression in mice muscle by in vivo electrically mediated siRNA delivery," Gene Therapy, Feb. 2005, vol. 12(3), pp. 246-251.
Gonzalez-Cadavid, N.F., et al., "Role of myostatin in metabolism," Current Opinion in Clinical Nutrition & Metabolic Care, Jul. 2004, vol. 7(4), pp. 451-457.
Gonzalez-Cadavid, N.F., et al., "Organization of the human myostatin gene and expression in healthy men and HIV-infected men with muscle wasting," Proc Natl Acad Sci USA, Dec. 1998, vol. 95, pp. 14938-14943.
Grobet, L., et al., "Modulating Skeletal Muscle Mass by Postnatal, Muscle-Specific Inactivation of the Myostatin Gene," Genesis, 2003, vol. 35, pp. 227-238.
Gronevik, E., "Gene expression and immune response kinetics using electroporation-mediated DNA delivery to muscle," J Gene Med, Feb. 2005, vol. 7(2), pp. 218-227.
Jackman, R.W., et al., "The molecular basis of skeletal muscle atrophy," Am J Physiol Cell Physiol, 2004, vol. 287, pp. C834-C843.
Lee, S.J., et al., "Regulation of muscle growth by multiple ligands signaling through activin type II receptors," Proc Natl Acad Sci USA, Dec. 13, 2005, vol. 102(50), pp. 18117-18122.
Lee, S.J., "Regulation of Muscle Mass by Myostatin," Annu Rev Cell Dev Biol, 2004, vol. 20, pp. 61-86.
Livak, K.J., et al., "Analysis of Relative Gene Expression Data Using Real-Time Quantitative PCR and the $2^{-\Delta\Delta}C_T$ Method," Methods, 2001, vol. 25, pp. 402-408.
Liu, M., et al., "Adeno-associated virus-mediated microdystrophin expression protects young mdx muscle from contraction-induced injury," Mol Ther, Feb. 2005, vol. 11(2), pp. 245-256.
Magee, T.R., et al., "Myostatin short interfering hairpin RNA gene transfer increases skeletal muscle mass," J Gene Med, 2006, vol. 8, pp. 1171-1181.
Magee, T.R., et al., "Gene Therapy of Erectile Dysfunction in the Rat with Penile Neuronal Nitric Oxide Synthase," Biology of Reproduction, Jul. 2002, vol. 67(1), pp. 20-28 (Corrected and republished in Biology of Reproduction, Sep. 2002, vol. 67(3), pp. 1033-1041).
McCroskery, S., et al., "Improved muscle healing through enhanced regeneration and reduced fibrosis in myostatin-null mice," J Cell Sci, 2005, vol. 118(15), pp. 3531-3541.
McMahon, J.M., et al., "Electroporation for Gene Transfer to Skeletal Muscles: Current Status," BioDrugs, 2004, vol. 18(3), pp. 155-165.
McPherron, A.C., et al., "Regulation of skeletal muscle mass in mice by a new TGF-beta superfamily member," Nature, May 1, 1997, vol. 387(6628), pp. 83-90.

(Continued)

*Primary Examiner* — Kimberly Chong
(74) *Attorney, Agent, or Firm* — Blakely Sokoloff Taylor & Zafman LLP

(57) ABSTRACT

A method comprising inhibiting myostatin expression or activity to increase muscle mass. Still further, methods for locally inhibiting myostatin expression or activity to reduce fibrosis are provided. The method comprises introducing a nucleotide sequence into a vector wherein the nucleotide sequence is expressed as a shRNA having a property to inhibit myostatin expression. The vector including the sequence may be delivered to a mammalian tissue. An electrical pulse may be applied across a point of delivery. A composition comprising a vector having a nucleotide sequence wherein the nucleotide sequence is expressed as a shRNA having a property to inhibit myostatin expression is further provided.

16 Claims, 16 Drawing Sheets

OTHER PUBLICATIONS

McPherron, A.C., et al., "Double muscling in cattle due to mutations in the myostatin gene," Proc Natl Acad Sci USA, Nov. 1997, vol. 94, pp. 12457-12461.

Mir, L.M., et al., "High-efficiency gene transfer into skeletal muscle mediated by electric pulses," Proc Natl Acad Sci USA, Apr. 1999, vol. 96, pp. 4262-4267.

Nishi, M., et al., "A missense mutant myostatin causes hyperplasia without hypertrophy in the mouse muscle," Biochem Biophys Res Commun, Apr. 26, 2002, vol. 293(1), pp. 247-251.

Patel, K., et al., "The function of myostatin and strategies of myostatin blockade—new hope for therapies aimed at promoting growth of skeletal muscle," Neuromuscul Disord, Feb. 2005, vol. 15(2), pp. 117-126.

Reddy, G.K., et al., "A simplified method for the analysis of hydroxyproline in biological tissues," Clin Biochem, Jun. 1996, vol. 29(3), pp. 225-229.

Reisz-Porszasz, S., et al., "Lower skeletal muscle mass in male transgenic mice with muscle-specific overexpression of myostatin," Am J Physiol Endocrinol Metab, 2003, vol. 285, pp. E876-E888.

Satkauskas, S., et al., "Slow Accumulation of Plasmid in Muscle Cells: Supporting Evidence for a Mechanism of DNA Uptake by Receptor-Mediated Endocytosis," Molecular Therapy, Oct. 2001, vol. 4(4), pp. 317-323.

Satkauskas, S., et al., "Mechanisms of in Vivo DNA Electrotransfer: Respective Contributions of Cell Electropermeabilization and DNA Electrophoresis," Molecular Therapy, Feb. 2002, vol. 5(2), pp. 133-140.

Schuelke, M., et al., "Myostatin Mutation Associated with Gross Muscle Hypertrophy in a Child," N Engl J Med, Jun. 24, 2004, vol. 350(26), pp. 2682-2688.

Seibler, J., et al., "Single copy shRNA configuration for ubiquitous gene knockdown in mice," Nucleic Acids Research, 2005, vol. 33(7), pp. e67 (10 pages).

Sioud, M., "Therapeutic siRNAs," Trends in Pharmacological Sciences, Jan. 2004, vol. 25(1), pp. 22-28.

Somia, N., et al., "Gene therapy: trials and tribulations," Nat Rev Genet, Nov. 2000, vol. 1(2), pp. 91-99.

Staron, R.S., et al, "Fiber type composition of four hindlimb muscles of adult Fisher 344 rats," Histochem Cell Biol, Feb. 1999, vol. 111(2), pp. 117-123.

Stegmeier, F., et al., "A lentiviral microRNA-based system for single-copy polymerase II-regulated RNA interference in mammalian cells," Proc Natl Acad Sci USA, Sep. 13, 2005, vol. 102(37), pp. 13212-13217.

Taylor, W.E., et al., "Myostatin inhibits cell proliferation and protein synthesis in $C_2C_{12}$ muscle cells," Am J Physiol Endocrinol Metab, 2001, vol. 280, pp. E221-E228.

Taylor, W.E., et al., "Alteration of gene expression profiles in skeletal muscle of rats exposed to microgravity during a spaceflight," Journal of Gravitational Physiology, Dec. 2002, vol. 9(2), pp. 61-70.

Thomas, M., et al., "Myostatin, a Negative Regulator of Muscle Growth, Functions by Inhibiting Myoblast Proliferation," J Biol Chem, Dec. 22, 2000, vol. 275(51), pp. 40235-40243.

Tobin, J.F., et al., "Myostatin, a negative regulator of muscle mass: implications for muscle degenerative diseases," Curr Opin Pharmacol, Jun. 2005, vol. 5(3), pp. 328-332.

Uchida, Y., et al., "Effective repetitive dystrophin gene transfer into skeletal muscle of adult mdx mice using a helper-dependent adenovirus vector expressing the coxsackievirus and adenovirus receptor (CAR) and dystrophin," J Gene Med, Aug. 2005, vol. 7(8), pp. 1010-1022.

Wagner, K.R., et al., "Loss of myostatin attenuates severity of muscular dystrophy in mdx mice," Ann Neurol, Dec. 2002, vol. 52(6), pp. 832-836, Abstract.

Wells, D.J., "Gene therapy progress and prospects: electroporation and other physical methods," Gene Therapy, Sep. 2004, vol. 11(18), pp. 1363-1369.

Whittemore, L.A., et al., "Inhibition of myostatin in adult mice increases skeletal muscle mass and strength," Biochem Biophys Res Commun, Jan. 24, 2003, vol. 300(4), pp. 965-971.

Wiener, P., et al., "Muscle-related traits in cattle: The role of the myostatin gene in the South Devon breed," Genet Sel Evol, 2002, vol. 34, pp. 221-232.

Wolfman, N.M., et al., "Activation of latent myostatin by the BMP-1/tolloid family of metalloproteinases," Proc Natl Acad Sci USA, Dec. 23, 2003, vol. 100(26), pp. 15842-15846.

Yin, C., et al., "Silencing heat shock factor 1 by small interfering RNA abrogates heat shock-induced cardioprotection against ischemia-reperfusion injury in mice," J Mol Cell Cardiol, Oct. 2005, vol. 39(4), pp. 681-689.

"pSilencer™ 2.1-U6 neo," http:www.ambion.com/techlib/misc/vectors/2.1_neo.html, Ambion Inc., 2006, 8 pages.

* cited by examiner

Normal tunica

Peyronie's disease

SEQUENCE LISTING

```
<160> NUMBER OF SEQ ID NOS: 10

<210> SEQ ID NO 1
<211> LENGTH: 2676
<212> TYPE: DNA
<213> ORGANISM: Mus musculus

<400> SEQUENCE: 1

gtctctcgga cggtacatgc actaatattt cacttggcat tactcaaaag caaaaagaag     60

aaataagaac aagggaaaaa aaaagattgt gctgattttt aaaatgatgc aaaaactgca    120

aatgtatgtt tatatttacc tgttcatgct gattgctgct ggcccagtgg atctaaatga    180

gggcagtgag agagaagaaa atgtggaaaa agaggggctg tgtaatgcat gtgcgtggag    240

acaaaacacg aggtactcca gaatagaagc cataaaaatt caaatcctca gtaagctgcg    300

cctggaaaca gctcctaaca tcagcaaaga tgctataaga caacttctgc caagagcgcc    360

tccactccgg gaactgatcg atcagtacga cgtccagagg gatgacagca gtgatggctc    420

tttggaagat gacgattatc acgctaccac ggaaacaatc attaccatgc ctacagagtc    480

tgactttcta atgcaagcgg atggcaagcc caaatgttgc tttttaaatt ttagctctaa    540

aatacagtac aacaaagtag taaaagccca actgtggata tatctcagac ccgtcaagac    600

tcctacaaca gtgtttgtgc aaatcctgag actcatcaaa cccatgaaag acggtacaag    660

gtatactgga atccgatctc tgaaacttga catgagccca ggcactggta tttggcagag    720

tattgatgtg aagacagtgt tgcaaaattg gctcaaacag cctgaatcca acttaggcat    780
```

-continued

```
tgaaatcaaa gctttggatg agaatggcca tgatcttgct gtaaccttcc caggaccagg    840
agaagatggg ctgaatccct ttttagaagt caaggtgaca gacacaccca agaggtcccg    900
gagagacttt gggcttgact gcgatgagca ctccacggaa tcccggtgct gccgctaccc    960
cctcacggtc gattttgaag cctttggatg ggactggatt atcgcaccca aaagatataa   1020
ggccaattac tgctcaggag agtgtgaatt tgtgttttta caaaaatatc cgcatactca   1080
tcttgtgcac caagcaaacc ccagaggctc agcaggccct tgctgcactc cgacaaaaat   1140
gtctcccatt aatatgctat attttaatgg caaagaacaa ataatatatg ggaaaattcc   1200
agccatggta gtagaccgct gtgggtgctc atgagctttg cattaggtta gaaacttccc   1260
aagtcatgga aggtcttccc ctcaatttcg aaactgtgaa ttcaagcacc acaggctgta   1320
ggccttgagt atgctctagt aacgtaagca caagctacag tgtatgaact aaaagagaga   1380
atagatgcaa tggttggcat tcaaccacca aaataaacca tactatagga tgttgtatga   1440
tttccagagt ttttgaaata gatggagatc aaattacatt tatgtccata tatgtatatt   1500
acaactacaa tctaggcaag gaagtgagag cacatcttgt ggtctgctga gttaggaggg   1560
tatgattaaa aggtaaagtc ttatttccta acagtttcac ttaatattta cagaagaatc   1620
tatatgtagc ctttgtaaag tgtaggattg ttatcattta aaaacatcat gtacacttat   1680
atttgtattg tatacttggt aagataaaat tccacaaagt aggaatgggg cctcacatac   1740
acattgccat tcctattata attggacaat ccaccacggt gctaatgcag tgctgaatgg   1800
ctcctactgg acctctcgat agaacactct acaaagtacg agtctctctc tcccttccag   1860
gtgcatctcc acacacacag cactaagtgt tcaatgcatt ttctttaagg aaagaagaat   1920
cttttttttct agaggtcaac tttcagtcaa ctctagcaca gcgggagtga ctgctgcatc   1980
ttaaaaggca gccaaacagt atcatttttt taatctaaat ttcaaaatca ctgtctgcct   2040
ttatcacatg gcaattttgt ggtaaaataa tggaaatgac tggttctatc aatattgtat   2100
aaaagactct gaaacaatta catttatata atatgtatac aatattgttt tgtaaataag   2160
tgtctccttt tatatttact ttggtatatt tttacactaa tgaaatttca aatcattaaa   2220
gtacaaagac atgtcatgta tcacaaaaaa ggtgactgct tctatttcag agtgaattag   2280
cagattcaat agtggtctta aaactctgta tgttaagatt agaaggttat attacaatca   2340
atttatgtat tttttacatt atcaacttat ggtttcatgg tggctgtatc tatgaatgtg   2400
gctcccagtc aaatttcaat gccccaccat tttaaaaatt acaagcatta ctaaacatac   2460
caacatgtat ctaaagaaat acaaatatgg tatctcaata acagctactt ttttatttta   2520
taatttgaca atgaatacat ttcttttatt tacttcagtt ttataaattg gaactttgtt   2580
tatcaaatgt attgtactca tagctaaatg aaattatttc ttacataaaa atgtgtagaa   2640
actataaatt aaagtgtttt cacatttttg aaaggc                             2676
```

<210> SEQ ID NO 2
<211> LENGTH: 21
<212> TYPE: DNA
<213> ORGANISM: Mus musculus

<400> SEQUENCE: 2

```
aagatgacga ttatcacgct a                                               21
```

<210> SEQ ID NO 3
<211> LENGTH: 63
<212> TYPE: DNA
<213> ORGANISM: Artificial sequence
<220> FEATURE:

<223> OTHER INFORMATION: Short hairpin DNA sequence sense strand based on SEQ ID NO. 1

<400> SEQUENCE: 3
gatccgatga cgattatcac gctattcaag agatagcgtg ataatcgtca tctttttttgg 60 aaa 63

<210> SEQ ID NO 4
<211> LENGTH: 1131
<212> TYPE: DNA
<213> ORGANISM: Rattus norvegicus

<400> SEQUENCE: 4
atgattcaaa aaccgcaaat gtatgtttat atttacctgt ttgtgctgat tgctgctggc 60
ccagtggatc taaatgagga cagtgagaga gaggcgaatg tggaaaaaga ggggctgtgt 120
aatgcgtgtg cgtggagaca aaacacaagg tactccagaa tagaagccat aaaaattcaa 180
atcctcagta aactccgcct ggaaacagcg cctaacatca gcaaagatgc tataagacaa 240
cttctgccca gagcgcctcc actccgggaa ctgatcgatc agtacgacgt ccagagggat 300
gacagcagtg acggctcttt ggaagatgac gattatcacg ctaccacgga aacaatcatt 360
accatgccta ccgagtctga ctttctaatg caagcggatg gaaagcccaa atgttgcttt 420
tttaaattta gctctaaaat acagtacaac aaagtggtaa aggcccagct gtggatatat 480
ctgagagccg tcaagactcc tacaacagtg tttgtgcaaa tcctgagact catcaaaccc 540
atgaaagacg gtacaaggta taccggaatc cgatctctga aacttgacat gagcccaggc 600
actggtattt ggcagagtat tgatgtgaag acagtgttgc aaaattggct caaacagcct 660
gaatccaact taggcattga aatcaaagct ttggatgaga atgggcatga tcttgctgta 720
accttcccag gaccaggaga agatgggctg aatccctttt tagaagtcaa agtaacagac 780
acacccaaga ggtcccggag agactttggg cttgactgtg atgaacactc cacggaatcg 840
cggtgctgtc gctaccccct cacggtcgat ttcgaagcct ttggatggga ctggattatt 900
gcacccaaaa gatataaggc taattactgc tctggagagt gtgaatttgt gttcttacaa 960
aaatatccgc atactcatct tgtgcaccaa gcaaacccca gaggctcggc aggcccttgc 1020
tgcacgccaa caaaaatgtc tcccattaat atgctatatt ttaatggcaa agaacaaata 1080
atatatggga aaattccagc catggtagta gaccggtgtg ggtgctcgtg a 1131

<210> SEQ ID NO 5
<211> LENGTH: 20
<212> TYPE: DNA
<213> ORGANISM: Rattus norvegicus

<400> SEQUENCE: 5
ggaaacaatc attaccatgc 20

<210> SEQ ID NO 6
<211> LENGTH: 20
<212> TYPE: DNA
<213> ORGANISM: Rattus norvegicus

<400> SEQUENCE: 6
atccacagct gggcctttac 20

<210> SEQ ID NO 7
<211> LENGTH: 1307
<212> TYPE: DNA
<213> ORGANISM: Rattus norvegicus -continued

<400> SEQUENCE: 7

```
gggggctctc tgctcctccc tgttctagag acagccgcat cttcttgtgc agtgccagcc     60
tcgtctcata gacaagatgg tgaaggtcgg tgtgaacgga tttggccgta tcggacgcct    120
ggttaccagg gctgccttct cttgtgacaa agtggacatt gttgccatca acgacccctt    180
cattgacctc aactacatgg tctacatgtt ccagtatgac tctacccacg gcaagttcaa    240
cggcacagtc aaggctgaga atgggaagct ggtcatcaac gggaaaccca tcaccatctt    300
ccaggagcga gatcccgcta acatcaaatg ggtgatgct ggtgctgagt atgtcgtgga    360
gtctactggc gtcttcacca ccatggagaa ggctggggct cacctgaagg gtggggccaa    420
aagggtcatc atctccgccc cttccgctga tgcccccatg tttgtgatgg gtgtgaacca    480
cgagaaatat gacaactccc tcaagattgt cagcaatgca tcctgcacca ccaactgctt    540
agccccccctg gccaaggtca tccatgacaa ctttggcatc gtggaagggc tcatgaccac    600
agtccatgcc atcactgcca ctcagaagac tgtggatggc ccctctggaa agctgtggcg    660
tgatggccgt ggggcagccc agaacatcat ccctgcatcc actggtgctg ccaaggctgt    720
gggcaaggtc atcccagagc tgaacgggaa gctcactggc atggccttcc gtgttcctac    780
ccccaatgta tccgttgtgg atctgacatg ccgcctggag aaacctgcca agtatgatga    840
catcaagaag gtggtgaagc aggcggccga gggcccacta aagggcatcc tgggctacac    900
tgaggaccag gttgtctcct gtgacttcaa cagcaactcc cattcttcca cctttgatgc    960
tggggctggc attgctctca atgacaactt tgtgaagctc atttcctggt atgacaatga   1020
atatggctac agcaacaggg tggtggacct catggcctac atggcctcca aggagtaaga   1080
aaccctggac cacccagccc agcaaggata ctgagagcaa gagagaggcc ctcagttgct   1140
gaggagtccc catcccaact cagcccccaa cactgagcat ctccctcaca attccatccc   1200
agaccccata acaacaggag gggcctgggg agccctccct tctctcgaat accatcaata   1260
aagttcgctg caccctcaaa aaaaaaaaaa aaaaaaaaaa aaaaaaa                 1307
```

<210> SEQ ID NO 8
<211> LENGTH: 21
<212> TYPE: DNA
<213> ORGANISM: Rattus norvegicus

<400> SEQUENCE: 8

```
atcactgcca ctcagaagac t                                               21
```

<210> SEQ ID NO 9
<211> LENGTH: 21
<212> TYPE: DNA
<213> ORGANISM: Rattus norvegicus

<400> SEQUENCE: 9

```
catgccagtg agcttcccgt t                                               21
```

<210> SEQ ID NO 10
<211> LENGTH: 21
<212> TYPE: DNA
<213> ORGANISM: Mus musculus

<400> SEQUENCE: 10

```
aaatgagggc agtgagagag a                                               21
```

METHOD FOR MODIFYING MYOSTATIN EXPRESSION

CROSS REFERENCE TO RELATED APPLICATIONS

This application claims priority from U.S. Provisional Patent Application Ser. No. 60/798,063, filed on May 4, 2006.

BACKGROUND

1. Field

Methods and compositions for modifying myostatin expression. In particular, methods and compositions which inhibit myostatin expression to increase muscle mass, prevent muscle loss and/or ameliorate fibrosis.

2. Background

Myostatin growth differentiation factor-8 (GDF-8 or myostatin) is a member of the transforming growth factor-beta (TGF-beta (β)) superfamily that negatively regulates muscle growth. (Patel K et. al., *Neuromuscul Disord.* 15:117-126 (2005)). The TGF-beta superfamily includes inhibins, activin, anti-müllerian hormone, and bone morphogenetic protein. TGF-beta acts to control proliferation, differentiation, and other functions in most cell types.

Genetic deletion (i.e. knock-out or KO) or inactivating mutations of myostatin in mice has been shown to result in excessive muscle growth measured by an increase in the size of existing muscle fibers (hypertrophy) and in genetic inactivation of myostatin expression in some mouse models measured by an additional increase in muscle number (hyperplasia). (McPherron et. al., *Nature* 387: 83-90 (1997)). Moreover, myostatin KO mice have exhibited increased proliferation of myoblasts that ultimately terminally differentiate and donate nuclei to myofibers. (Thomas et al., *J Biol Chem* 275: 40235-40243 (2000)). In both the myostatin KO mouse model and in naturally occurring bovine mutant cattle breeds (Belgian Blue, Piedmontese, and others), loss of myostatin activity has been shown to increase muscle mass. (Patel et. al., *Neuromuscul Disord.* 15:117-126 (2005)). A similar 'muscling' phenotype has further been documented in a child with inactivating mutations for both myostatin alleles. (Schuelke et al, *N Engl J Med* 350: 2682-2688 (2004)). Conversely, myostatin protein over-expression has been shown to decrease muscle mass and fiber size in a transgenic mouse model. (Reisz-Porszasz et al, *Am J Physiol Endocrinol Metab* 285: E876-E888 (2003)).

In addition to its role as a negative regulator of muscle mass, myostatin has recently been implicated in fibrosis. In particular, in vivo long-term administration of myostatin antibodies to an mdx mouse, a model of muscle dystrophy, has been shown to not only enhance myofiber regeneration but also reduce the considerable muscle fibrosis observed in these animals. (Bogdanovich et. al., *Nature* 420: 418-421 (2002)). Additionally, the myostatin KO mouse shows improved muscle healing and reduced fibrosis in an acute muscle injury model (McCroskery et al., *J Cell Sci* 118: 3531-3541 (2005) and an mdx-myostatin null double mutant model. (Wagner et. al., *Ann Neural* 52: 832-836 (2002)).

In view of these findings, attempts have been made to increase muscle mass by controlling the expression of myostatin systemically. In one study, injections of a protease resistant propeptide form of myostatin, which cannot be processed into the putative mature myostatin but can bind the one already produced, were administered weekly over the period of one month. (Wolfman et al, *Proc Natl Acad Sci USA* 100: 15842-15846 (2003)). As a result of the weekly injections, muscle mass increased by 25 percent (%). (Wolfman et al, *Proc Natl Acad Sci USA* 100: 15842-15846 (2003)). In another study, daily injections of anti-myostatin antibodies were administered into the peritoneum for one month resulting in a muscle mass increase of 20%. (Whittemore et al, *Biochem Biophys Res Commun* 300: 965-971 (2003).

Although these studies support the notion that systemically blocking myostatin activity might be therapeutically efficacious in humans, the blockade during embryonic development is associated with substantial side effects. The Belgian Blue cattle and other mutant breeds demonstrate reduced female fertility and an increase in caesarian section birthing due to a decreased ability to carry a fetus to term. (Whittemore et al, *Biochem Biophys Res Commun* 300: 965-971 (2003)). In addition, these animals abnormally overheat during exercise, a process associated with the excessive musculature. (Chupin D., Analysis of reproduction problems in double muscle females. In: King J W B, Menissier, F. editors. Muscle hypertrophy of genetic origin and its use to improve beef production). Transgenic myostatin KO mice also exhibit some decreased fertility. (Patel K et. al., *Neuromuscul Disord.* 15:117-126 (2005)).

Still further, there are several problems associated with the general inhibition of myostatin activity by antibodies. In particular, such techniques may be difficult to sustain long term, may lead to undesirable immune responses, and may affect tissues other than the muscle, where an endogenous basal production of myostatin could still be functionally significant.

Delivery of gene constructs into muscle using viral and plasmid based protocols as well as the direct injection of naked DNA has further been documented. Viral based protocols have utilized adeno-associated viruses to express microdystrophin complimentary DNA (cDNA) and helper-dependent adenoviruses to express the full dystrophin gene. Direct injection of naked DNA into muscle without the use of an adjuvant to facilitate uptake of DNA into cells, however, has been found to be relatively poor, possibly due to DNA uptake requiring slow endocytotic mechanisms.

BRIEF DESCRIPTION OF THE DRAWINGS

The following illustration is by way of example and not by way of limitation in the figures of the accompanying drawings in which like references indicate like elements. It should be noted that references to "an" or "one" embodiment in this disclosure are not necessarily to the same embodiment, and such references mean at least one.

DETAILED DESCRIPTION

Figure 1:
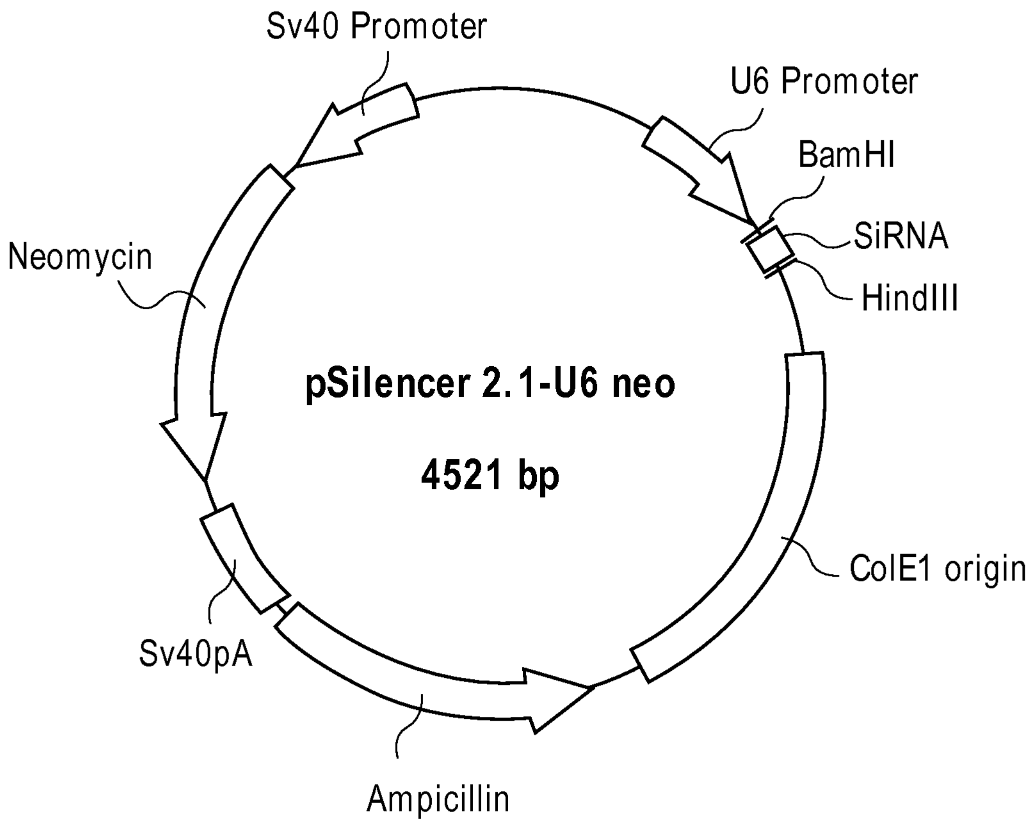
FIG. 1 shows the structure of a pSILENCER® 2.1-U6 neo expression vector.

Techniques for modifying myostatin expression are described herein. Such techniques may be particularly useful in enhancing muscle growth and treating various conditions and diseases affecting muscle tissues, such as smooth and skeletal muscle tissue, as well as other mammalian tissues. In particular, techniques described herein may be useful in increasing muscle mass, preventing loss of muscle mass and treating conditions involving loss of muscle mass or the fibrosis occurring during loss of muscle mass. Exemplary conditions and diseases may include muscle atrophy that occurs with aging, skeletal muscle atrophy and dystrophy in sarcopenia of old age, caquexia, congenital and hereditary conditions of the skeletal muscle, diabetes, kidney dialysis, stroke, spinal cord injury, spinal muscular atrophy, peripheral nerve injury, skeletal muscle injury, burn injury, prolonged immobilization (casting or bed resting), osteoarthritis, rheumatoid arthritis, prolonged corticosteroid therapy, diabetes, poliomyelitis, amyotrophic lateral sclerosis, Guillain-Barre syndrome, muscular dystrophy (Duchenne's and others), myotonia congentia, cachexia, HIV related muscle wasting, loss due to microgravity, skeletal muscle disuse, neuropathy leading to skeletal muscle wasting, hyperglycemia, carpal tunnel syndrome, chronic infection, tuberculosis, Addison's disease, anorexia nervosa, dermatomyositis, inclusion body myositis, incontinentia pigmenti, intercostal neuralgia, legg-calve perthes disease, multifocal motor neuropathy, nephrotic syndrome, osteogenesis imperfecta, post-polio syndrome, Tay Sachs syndrome or any general or localized skeletal muscle loss condition. The techniques described herein may further be used to treat fibrosis occurring during muscle atrophy such as muscular dystrophy, or any general or localized muscle loss condition having fibrosis as a component of the condition. Other applications relating to smooth muscle tissue treatments may include, increasing smooth muscle mass, increasing penile size, decreasing smooth muscle fibrosis and increasing smooth muscle of the corpora cavernosa of the penis.

In one aspect, techniques described herein include any method by which myostatin expression and/or activity is blocked or otherwise inhibited in any tissue such that size is increased and/or fibrosis is reduced or otherwise counteracted, including but not limited to Peyronie's disease plaque, penile corporal fibrosis, penile veno-occlusive dysfunction, Dupuytren's disease nodules, vaginal fibrosis, clitoral fibrosis, female sexual arousal disorder, abnormal wound healing, keloid formation, general fibrosis of the kidney, bladder, prostate, skin, liver, lung, heart, intestines or any other localized or generalized fibrotic condition, vascular fibrosis, arterial intima hyperplasia, atherosclerosis, arteriosclerosis, restenosis, cardiac hypertrophy, hypertension or any condition characterized by excessive fibroblast cell proliferation or deposition of collagen and extracellular matrix in the blood vessels and/or heart.

Still further, techniques described herein may include any method by which myostatin expression and/or activity is blocked or otherwise inhibited in skeletal muscle such that its mass is increased and fibrosis is counteracted, including but not limited to skeletal muscle atrophy and dystrophy in sarcopenia of old age, kidney dialysis, burns, diabetes, caquexia, prolonged immobilization, congenital and hereditary conditions of the skeletal muscle.

In other embodiments, techniques described herein may include any method by which myostatin expression and/or activity is inhibited to increase smooth muscle mass. In one aspect, increasing the smooth muscle mass includes increasing penis size.

Methods may include those which directly block myostatin expression and/or its activity using agents which may include, but are not limited to antibodies against myostatin, proteins that bind to and inhibit myostatin activity and/or their encoding cDNAs, inhibiting peptides and/or their encoding cDNAs, shRNA targeting myostatin, siRNA targeting myostatin, agents that inhibit the expression of myostatin, agents that inhibit the activity of myostatin, or ligands that bind to the myostatin/activin receptor. Additional methods may include, but are not limited to, modulating the expression or activity of proteins and/or mucopolysaccharides that regulate the activity of myostatin. Modulation could include antibodies against these myostatin regulating proteins, proteins that bind to and modulate the regulatory protein activity, inhibiting peptides, shRNA, siRNA, inhibitor or activator agents that block or enhance the expression of the myostatin regulating proteins, agents that modulate the activity of myostatin regulating proteins. Examples may include increasing the expression or activity of follistatin or related proteins, or administering it directly.

In some embodiments, the method of inhibiting myostatin expression and/or activity may include local inhibition of myostatin by delivering an agent at a point within the tissue region where myostatin inhibition is desired. In other embodiments, the method of inhibiting myostatin expression and/or activity may include systemic inhibition of myostatin by delivering an agent to a tissue near (e.g., proximal to) the tissue region where myostatin inhibition is desired or delivering the treatment agent more remotely.

Therapeutic uses may include, but are not limited to, the enlargement of penis size, or in the treatment or prevention of small penis size, cavernosal smooth muscle myopathies, congenital micropenis and other genetic abnormalities, effects of hypogonadism on penile size, penile trauma, hypospadias, transsexual penile construction, penile amputation, penile cancer, Peyronie's disease and vasculogenic erectile dysfunction related to penile fibrosis.

In one embodiment, the method may be a vector based therapy. Briefly, the term "vector" generally refers to a vehicle for delivering genetic material to a cell. A vector may include, for example, a virus reengineered to deliver a gene to a target cell or a DNA construct such as a plasmid or a bacterial artificial chromosome having an origin of replication. The term "plasmid" generally refers to a typically circular double-stranded DNA molecule separate from chromosomal DNA which is capable of autonomous replication. Plasmid vectors may be produced in large quantities under strict quality control, have relatively low toxicity, do not integrate into chromosomal DNA, and can accommodate the expression of large genes or even multiple genes. Muscle tissue may be readily transduced with plasmid DNA and gene expression achieved on the order of several weeks. The term "transduced" or "transduction" as used herein generally refers to a process by which genetic material, e.g. DNA, is inserted into a cell.

In one aspect, a nucleotide sequence having a property to inhibit myostatin expression may be incorporated into the vector and then delivered to a mammalian tissue to inhibit myostatin expression. The nucleotide sequence may be a myostatin targeting DNA sequence capable of being processed by a cell into a short interfering RNA (siRNA). The term "short interfering RNA" or "siRNA" as used herein refers to small or short RNA sequences that may have, for example, around 20-25 base pairs (bps). siRNAs are capable of causing interference and may cause post transcriptional silencing of specific genes in cells. Post transcriptional silencing, also referred to as RNA interference (RNAi), is a mechanism characterized by the presence of double-stranded RNA (dsRNA) fragments which interfere with expression of a particular gene which shares a homologous sequence with the dsRNA. dsRNA induced gene silencing involves a two-step mechanism in which first the dsRNA silencing trigger is recognized by a RNase III family nuclease called Dicer which cleaves the dsRNA into a 21-23 nucleotide siRNA. The siRNA is then incorporated into a nuclease complex, RISC, which identifies substrates through their homology to siRNA and targets these cognate mRNAs for destruction. The suppressive effects of siRNAs, however, tend to be of a limited duration.

A short hairpin RNA (shRNA) may be processed by a cell into an siRNA which may in turn induce RNAi of a target gene. The term "short hairpin RNA" or "shRNA" as used herein refers to an RNA sequence that forms a hairpin loop which may further be used in gene expression silencing. A DNA sequence template for the shRNA may be incorporated into a vector, for example a viral or plasmid vector, and expressed to provide continuous long-term expression from RNA polymerase III (pol III (U6)) or RNA polymerase II (pol II) promoters in cell culture (Brummelkamp et. al., *Science* 296: 550-553 (2002)), thus overcoming some of the limitations associated with siRNA. RNA polymerase facilitates the transcription initiation process by copying a DNA sequence to produce a complementary RNA.

Thus, in one aspect, the nucleotide sequence incorporated into the vector may be a myostatin targeting DNA sequence capable of being expressed as an shRNA within a target cell and then processed by the cell into an siRNA. Once inside a cell, the vector enters the nucleus and the myostatin targeting siRNA sequence is produced from the plasmid myostatin targeting DNA sequence by the cell. The siRNA will specifically bind to myostatin mRNA and target it for degradation. Loss of myostatin mRNA leads to a decrease in myostatin protein, which in turn leads to increased inhibition of myostatin activity. This inhibition of myostatin activity, results in increased muscle cell mass (hypertrophy) and it is further believed myostatin inhibition results in increased muscle cell number (hyperplasia). In one embodiment, the target cell may be that of any mammalian tissue which may be regulated or otherwise modified by myostatin expression. In one aspect, the target cell may be that of a skeletal muscle tissue. In other embodiments, the target cell may be that of a smooth muscle tissue, such as, for example, smooth muscle of the corpora cavernosa of the penis.

The vector containing the myostatin targeting DNA sequence capable of being expressed as an shRNA in vivo (generally referred to herein as "the shRNA vector construct"), may be delivered to a point within a mammalian tissue where it will locally inhibit myostatin activity. Such an shRNA based gene therapy may be beneficial in treating and/or balancing the deleterious effects of numerous conditions and diseases affecting muscle tissue. Although myostatin shRNA gene therapy may not correct the underlying pathophysiology of many of the conditions previously discussed, which remain relatively unknown, it may counterbalance the effects by stimulating satellite cell activation and myofiber growth.

In one embodiment, the shRNA myostatin targeting sequence, and in turn the nucleotide sequence to be incorporated into the vector, may be identified by first determining a siRNA sequence capable of inhibiting myostatin expression. In this aspect, a myostatin gene sequence is initially identified. The myostatin gene sequence may be derived from mouse, rat, cow, human, rabbit, cow, macaque or baboon. The myostatin gene sequence may further be derived from chicken, turkey, fish and other suitable species. For example, in one embodiment, a mouse myostatin gene sequence is identified and referred to herein as SEQ ID NO:1 (GenBank Accession Nos. NM_010834). Regions of SEQ ID NO:1 may be examined to identify specific regions which are inhibited by siRNAs and analyzed as illustrated below in Example 1 to determine which regions have the best myostatin inhibitory activity. The siRNA sequences which are found to target myostatin may then be transfected into human embryonic kidney (HEK293) cells and identified for myostatin silencing (inhibition) by, for example, western blot. Corresponding DNA sequences expressing shRNAs that may be processed by the cell into the siRNA sequence found to inhibit myostatin expression may then be cloned into, for example, plasmid or viral expression vectors. Uptake of the plasmid may be examined by beta-galactosidase expression and myostatin expression may be determined by, for example, real-time PCR and western blotting.

Delivery of a vector including the DNA sequence for the shRNA sequence having a property to inhibit myostatin expression to a point within the mammalian tissue may be accomplished by delivering the vector in any form suitable for delivery to mammalian tissues, including but not limited to, skeletal muscle tissue and smooth muscle tissue. In one aspect, the shRNA vector construct may be part of a composition including, for example, a suspension, a solution, or an emulsion in an oily or aqueous vehicle suitable for delivery to a desired mammalian tissue orally, by injection or topically. In one aspect, the shRNA vector construct may be part of an isotonic solution that is otherwise harmless to the tissue or cells. In some embodiments, the composition may take the form of a lotion, cream or other similar substance suitable for topical application. Suspending, stabilizing and/or dispersing agents may be included in the composition.

In still further embodiments, the shRNA vector construct may be delivered in the form of a pharmaceutical composition. Pharmaceutical compositions according to the present invention may be formulated by standard techniques using one or more physiologically acceptable carriers or excipients. Representatively, the pharmaceutical composition including the shRNA vector construct may be formulated and administered, by, for example, intramuscular, epicutaneous, intravenous or intraperitoneal techniques. In some embodiments, an intravenous or intraperitoneal liposomal formulation, combined with muscle specific gene promoters according to a repeated injection paradigm may be utilized. It is believed that a tissue specific and time regulable promoter may induce effects exclusively in the muscle when given systemically and these effects may be started and interrupted at will.

In one embodiment, an amount of the shRNA vector construct delivered to the desired tissue is at equivalent dosages per unit of body weight corrected by surface area as a dosage administered to a rodent. In this aspect, the formulation may include the shRNA vector construct suspended in a solution at a concentration of approximately 1 microgram/microliter (μg/μl). For example, the formulation may include the shRNA vector construct suspended in a sterile 0.9% NaCl saline isotonic solution at a concentration of 1 μg/μl. In this aspect, a single dose may be 100 μls of the solution such that a single dosage includes 100 μgs of the shRNA vector construct. It is further contemplated that a single dose may be any volume amount found suitable for the method of delivery to be used (e.g. oral, topical or injection). Still further, the volume amount of a single dose may be selected based on the volume of fluid a selected tissue may accommodate. For example, it may be desirable to inject the formulation into a small tissue region that is unable to accommodate (i.e. absorb) 100 μl s of fluid, thus the volume amount of a single dose may be less than 100 μls and the concentration of the shRNA vector construct in the formulation may be altered so that a desired amount of the shRNA vector construct may be delivered at the reduced volume.

In other embodiments, the amount of the shRNA vector construct delivered to the tissue may be at a lower dosage then a dosage administered to a rodent. In this aspect, the formulation may include the shRNA vector construct suspended in a sterile 0.9% NaCL saline isotonic solution at a concentration of between approximately 0.5 μg/μl and approximately 1 μg/μl. For example, the formulation may include a sterile 0.9% NaCL saline isotonic solution at a concentration of 0.5 μg/μl. In this aspect, a single dose may be 100 μls of the formulation (50 pigs of the shRNA vector construct).

Alternatively, the amount of the shRNA vector construct delivered to the tissue may be at a higher dosage then a dosage administered to a rodent. In this aspect, the formulation may include the shRNA vector construct suspended in a solution at a concentration of between approximately 1 μg/μl to approximately 10 μg/μl. In other embodiments, the formulation may include the shRNA vector construct at a concentration of between approximately 1 μg/μl to approximately 5 μg/μl. Representatively, the formulation may include a sterile 0.9% NaCL saline isotonic solution at a concentration of 5 μg/μl. In this aspect, a single dose may be 100 μls of the formulation (500 μgs of the shRNA vector construct). Although specific amounts of the shRNA vector construct to be delivered to the tissue are disclosed, it is contemplated that the amount of vector construct delivered may vary and include any amount sufficient to produce a measurable result, for example, a measurable increase in muscle mass or reduction in fibrosis.

In one aspect, the shRNA vector construct may be delivered to mammalian tissue by way of an injection to, for example, a muscle tissue, according to a variety of techniques and devices, including but not limited to a bolous injection or continuous infusion. Such localized administration to one or a few easily accessible muscles may be particularly desirable in the case of non-systemic conditions affecting only specific muscles, such as in regeneration after injury or in combating atrophy during cast immobilization, where both the time-course and the quality of repair may be improved by counteracting temporarily local myostatin expression. It is further contemplated that the shRNA vector construct may be injected in multiple sites and could be injected repeatedly to maintain myostatin inhibition. In other embodiments, systemic administration according to standard techniques (e.g. intravenous injections) may be used to deliver the vector to the mammalian tissue. In other embodiments, oral (e.g. inhaler, capsule or oral solution) or topical (e.g. lotion or cream) administration modalities may be used to deliver the shRNA vector construct to the tissue. It is further contemplated that other modalities of delivery may be utilized according to the desired effect, tissue to be treated, type of condition and/or disease being treated.

In some embodiments, a variety of techniques may be employed to increase cell uptake of the shRNA vector construct. In one embodiment, intramuscular electroporation, sometimes referred to as electro-gene transfer, may be used to increase uptake. Electroporation increases the permeability of cell membranes through the application of an electrical field. The electrical field causes transient pore formation in the membranes thereby allowing for uptake of plasmid DNA. In this aspect, electroporation may be achieved, for example, by positioning a set of electrodes of the electroporator on each side of the tissue to be electroporated. An amount of the shRNA vector construct may then be, for example, injected between the electrodes and an electroporation pulse may be delivered to the tissue at a sufficient strength and duration so as not to cause apoptosis and/or necrosis to the cells. Alternatively, the shRNA vector construct may be delivered to the desired tissue before the electrodes are positioned on the skin. Representative settings may be approximately 100 V (voltage), 40 millisecond (msec) (duration), 8 pulses per second (frequency), 1 second (interval). It is further contemplated that the voltage and other settings may be adjusted based upon factors such as the distance between the electrodes and tissue to be electroporated. The electrodes may be any electrode configuration found suitable for applying an electrical field to a tissue having the shRNA vector construct therein. In some embodiments, the electrodes may be non-needle electrode patches or caliper style electrodes that may be placed on the skin adjacent to the tissue to be treated such that the electroporation pulse may be applied non-invasively through the skin. Alternatively, the electrodes may be needle-style electrodes such that the needle is inserted through the skin and the electroporation pulse applied within the tissue region beneath the skin.

In still further embodiments, cellular uptake of the shRNA vector construct may be increased by mixing the shRNA vector construct with a carrier such as, for example, a dimethyl sulfoxide (DMSO) found to easily penetrate skin and other membranes. Alternatively, the shRNA vector construct may be mixed with an agent such as an adjuvant having a property to facilitate cellular uptake of the shRNA vector construct when delivered to a desired tissue region.

Embodiments disclosed herein may be illustrated by use of the following non-limiting examples:

Example I

1. Identification of a siRNA Targeted Against Myostatin and Construction of a Plasmid-Based Gene Transfer Vector The identification of a siRNA sequence which may inhibit myostatin may be carried out by standard techniques. In one aspect, an siRNA sequence which inhibits myostatin may be identified using the web-based siRNA target finder and design tool available on the website www.ambion.com provided by Ambion Inc., Austin, Tex. Once potential siRNA targets are identified, double stranded siRNAs may be transcribed "in vitro" using a standard silencer siRNA construction kit, such as that available from Ambion Inc, Austin, Tex. and tested for inhibitory activity. The best inhibitory siRNA may then be cloned into a pSILENCER® 2.1 U6-neo plasmid vector ($2^{nd}$ version, Ambion, Inc., Austin, Tex.) as a short hairpin DNA sequence.

In one embodiment, five regions of the sequence identified above as SEQ ID. NO.: 1 (GenBank Accession Nos. NM_010834) may be identified as likely to have inhibitory activity by siRNAs, including, but not limited to those at nucleotide position [target #], 175[#4], 207[#8], 426[#26], 647[#45], and 1064[#72]. In one embodiment, a sequence located at 426[#26], represented by the sequence 5'-AAGATGACGATTATCACGCTA-3' (SEQ ID NO.: 2), may be selected as the inhibitory siRNA (myostatin siRNA26) target region for further testing. In this aspect, the siRNA26 sequence may be cloned into the pSILENCER® 2.1 U6-neo plasmid vector as a short hairpin DNA sequence. The hairpin DNA sequence may be represented by the sequence 5' sense strand: 5'-GATCCGATGACGATTATCACGCTATTCAAGAGATAGCGTGATAATCGTCATCTTT TTTGGAAA-3' (SEQ. ID NO.: 3). Major factors included in the vector may be, for example, a BamHI DNA restriction site, sense-strand, 9 nucleotide loop, anti-sense strand, RNA polymerase III terminator, and HindIII DNA restriction site 5' to 3.' A representative pSILENCER® vector map which may include, for example, SEQ ID NO.: 3 at a region labeled siRNA, a U6 promoter, SV40 early promoter, neomycin, SV40 early pA signal, ampicillin and ColE1 origin is generally illustrated by FIG. 1.

In addition, a shRNA 'randomer' sequence, provided with the pSILENCER® kit and known not to block any mammalian mRNA, may also be prepared. To test for silencing, the pSILENCER® 2.1-U6 neo-myostatin siRNA plasmid construct or pSILENCER® 2.1-U6 neo-randomer plasmid may be co-transfected with pcDNA3.1-myostatin (each 1 microgram (μg) per well, 6 well plate) into HEK293 cell cultures using lipofectamine 2000 (1:1 DNA:liposome ratio) for 48 hours and assayed by anti-myostatin antibody western blotting.

2. In Vivo Injection and Electroporation of Plasmid Constructs

Plasmids may be grown up in *E. coli* strain DH5-alpha (α) and purified using an Endo-free Maxi Kit (Qiagen, Valencia, Calif.). Plasmids may be quantified by spectrophotometry and prepared in 0.9% NaCl saline solution at a concentration of 1 μg/μl. Male Fisher 344 rats, 2-3 months old, may be maintained under controlled temperature and lighting, and treated according to NIH regulations.

Animals (e.g., n=9) may be anesthetized and maintained during the procedure with isoflurane gas. Rats may be sequentially laid out in a supine position and the hair covering the front lower leg may be removed with animal clippers. Using a 29 gauge needle, 100 μls of plasmid solution (100 μgs total) may be injected through the skin into the underlying tibialis anterior muscle. In some aspects, two injections may be given, approximately half of the solution in each site (50 μls) separated by half a centimeter. The plasmid including the DNA sequence which will be expressed as the myostatin inhibiting shRNA in vivo may be injected into the left leg through the skin and a randomer negative control shRNA plasmid injected into the right leg. Immediately following injection, electroporation may be applied across the injection site using a 0.5 cm platinum needle electrode coupled to a Electro Square Porator Model ECM830 (Gentronix, San Diego, Calif.). Settings may be 100 V (voltage); 40 msec (duration); 8 pulses per second (frequency); 1 second (interval); unipolar (polarity). The above-referenced conditions are similar in some respects to conditions described in an article disclosing a protocol in skeletal muscle by Mir et al, *Proc Natl Acad Sci USA* 96: 4262-4267 (1999) which was modified based on Faurie et al., *DNA Cell Biol* 22: 777-783 (2003). Electrical pulses may be applied twice, with the electrode needles parallel to the muscle fibers for the first pulsing and perpendicular across the fibers for the second pulsing.

For examining the persistence and spread of a reporter plasmid vector into the tibialis anterior muscle, pSport-betagal (Invitrogen, Carlsbad, Calif.) may be injected into the tibialis anterior skeletal muscle of six rats (2 rats per time point) in the same dosage and treatment as described above. The rats may be sacrificed at 1, 2, and 4 weeks and tissue dissected and frozen for later analysis.

3. Histochemistry, Immunohistochemistry and Image Analysis

In one aspect, the above described treated animals may be euthanized using a $CO_2$ gas chamber. Tibialis anterior muscles may be excised from the limb using the ligaments as anatomical reference and electrode marks as a reference to gene electro-transfer. The muscles may be divided into three longitudinal pieces. One portion may be placed in RNALater® (Ambion Inc., Austin, Tex.), the second piece may be frozen immediately in liquid nitrogen and the third piece may be fixed in formalin for 24 hours. After fixation, the tissues may be transferred to 70% ethanol until further processing for paraffin embedding.

Transversal five μm sections may be cut in a microtome and the sections collected onto slides. The sections may deparaffinized, rehydrated and stained with Trichome Stain (Masson) (Sigma Chemical Co., St. Louis, Mo.) following the manufacturer instructions. The Trichome Stain (Masson) facilitates differentiation between the skeletal muscle and collagen fibers. Adjacent sections used for Trichome Stain (Masson) staining may be utilized for the determination of PAX7 protein by immunohistochemistry with anti-PAX7 monoclonal antibody (Hybridoma Bank, University of Iowa, Iowa City, Iowa). Sections may be deparaffinized and hydrated and treated by antigen retrieval, micro waving the slides in antigen unmasking solution (Vector Laboratories, Burlingame, Calif.), quenched in 3% $H_2O_2$—PBS and blocked with horse serum (Vector Laboratories, Burlingame, Calif.), and incubated with primary anti-PAX7 Immunoglogulin G (IgG) antibody at 1:100 dilution overnight at 4° C., followed by incubation with biotinylated horse anti-mouse IgG (Vector Laboratories, Burlingame, Calif.) for 40 minutes. Negative controls may be used which omit the first antibodies or may be replaced by an IgG isotype at the same concentration as the first antibodies. Color development may be performed with avidin-biotin (Vector Laboratories, Burlingame, Calif.) followed by 3,3 diamino-benzidine (DAB) (Sigma Chemical Co., St. Louis, Mo.), and counter-stained with hematoxylin.

Quantitative evaluation of stained sections for myofiber size may be performed using the ImagePro 4.01 program software (Media Cybernetics, Silver Spring, Md.), coupled to an Olympus BHS microscope equipped with a Spot RT digital camera, calibrated for spatial measurement and intensity. Fiber size may be determined by measuring the area of each transversal myofiber per a fixed area. Approximately 100 myofibers may be measured for each tibialis anterior tissue sample (6-8 fields/tissue section). For immunohistochemistry, the number of PAX-7 positively stained cells may be determined, by counting the number of positive cells per field. A total of 10 fields at 400× magnification may be counted per section. Quantitative evaluation may be performed blinded as to the sample type.

Beta-galactosidase staining may further be performed. In this aspect, the tibialis anterior muscle may be dissected and fixed in formalin for 4 hours. The samples may be rinsed overnight in permeabilization buffer (100 mM sodium phosphate, pH 7.3, 2 mM $MgCl_2$, 0.01% sodium deoxycholate, 0.02% NP-40). Staining for beta-galactosidase may be performed with 0.1% X-gal in permeabilization solution supplemented with 5 mM each $K_3Fe(CN)_6$ and $K_4Fe(CN)_6$ for 15 hours at 37 degrees Celsius (° C.) with agitation. After staining, the muscles may be embedded in Optimal Cutting Temperature (O.C.T.) compound (Sakura, Torrance, Calif.) and frozen. 50 µm tissue sections may be cut in a cryostat (Leica, Houston, Tex.) and the frozen tissue blocks photographed using a digital camera (FinePix 40i, FujiFilmUSA, Elmsford, N.Y.).

4. Determination of Myostatin Gene Expression, Protein Expression and Collagen Content In one aspect, expression of myostatin mRNA may be measured by real time RT-PCR. In this aspect, real time RT-PCR analysis may be performed on isolated tibialis anterior muscle. Total RNA may be isolated from frozen tissue using known techniques, including but not limited to, the Trizol procedure (Invitrogen Co., Carlsbad, Calif.). 0.2 µg from myostatin shRNA treated tissue (n=9), and randomer shRNA treated tissue may be reverse transcribed using Superscript III RNase $H^-$ reverse transcriptase (Invitrogen Co., Carlsbad, Calif.) and random hexamers (0.25 µg) following the manufacturer's protocol. Real-time PCR may be performed with rat myostatin specific primers spanning an intron to exclude DNA contamination. Primers based on the rat myostatin gene (for example, SEQ. ID NO: 4, Genbank Accession No. NM_019151) may include Forward: 5' GGAAACAATCATTACCATGC 3' (nucleotide position 348-367, SEQ. ID NO: 5) and Reverse: 5' ATCCACAGCTGGGCCTTTAC 3' (nucleotide position 457-476, SEQ ID NO 6). Reaction conditions may be based on the qPCR Mastermix Plus for SYBR® Green I kit protocol (Eurogentec, San Diego, Calif.). In particular, 1 µl of RT reaction may be added in a reaction mix consisting of 1×qPCR Mastermix Plus (buffer and dNTPs), and forward and reverse primers at 300 µM each in a 25-ul reaction. Real-time RT-PCR was done in a ABI Prism 7000 Sequence Detection System (Applied Biosystems, Warrington, UK). The control reference gene may be GAPDH (for example, SEQ ID NO: 7, Genbank Accession No. BC059110). GAPDH primers may be Forward: 5' ATCACTGCCACTCAGAAGACT 3'(nucleotide position 611-631, SEQ ID NO: 8), and Reverse: 5' CATGCCAGTGAGCTTCCCGTT 3' (nucleotide position 743-763, SEQ ID NO: 9). Each RT may be amplified in triplicate and ratio results expressed as the mean+/−SEM. Relative ratios were calculated based on the $2^{-\Delta\Delta C}{}_T$, method (Livak et. al., *Methods* 25: 402-408 (2001).

Myostatin, myosin heavy chain type II (MHCII), and GAPDH protein determinations may be performed by western blotting. For myostatin, a monoclonal antibody for cell protein extracts and a polyclonal antibody for muscle tissue extracts based on preliminary data examining which antibody yielded the most specific binding reaction (data not shown) may be used. For detecting mouse myostatin expressed from HEK293 cells transfected with pcDNA3.1-myostatin, 40 µgs of protein extract was run on 12% gel electrophoresis, using a 1:1000 mouse monoclonal anti-myostatin primary antibody that was custom made against a peptide as discussed in Artaza et al. Endocrinology 146: 3547-3557 (2005). A secondary anti-mouse antibody (BD Biosciences, San Jose, Calif.) may be diluted 1:5000 and linked to horseradish peroxidase. For muscle tissue extracts (50 µgs), a custom polyclonal anti-myostatin antibody may be used at a dilution of 1:200. (Artaza et al. Endocrinology 146: 3547-3557 (2005)). For other proteins, 1:200 mouse monoclonal anti-MHC type II antibody (Novocastra Laboratories, Newcastle, UK), or 1:10000 anti-GAPDH monoclonal antibody (Chemicon International, Temecula, Calif.) may be used. The washed membranes may be incubated with 1:1000 dilution of secondary antibody linked to horseradish peroxidase. Immunoreactive bands may be visualized by using a SuperSignal West Pico chemiluminescence detection system (Pierce Biotechnology Inc., Rockford, Il). Band intensities may be estimated by densitometry and corrected by the respective GAPDH band intensities.

Collagen determination by hydroxyproline may be performed as described by Reddy et. al., *Clin Biochem.* 29: 225-229 (1996) and Ferrini et al., *Nitric Oxide* 6: 283-294 (2002). In particular, aliquots of the initial homogenates of total muscle tissue, without any centrifugation step, may be hydrolyzed with 2N sodium hydroxide (NaOH) for 30 min at 120° C., followed by the estimation of hydroxyproline by a modification of the Neumann and Logan's reaction using Chloramine T reagent followed by Erlich's reagents. The color developed may be compared by a hydroxyproline standard curve measured at 535 nm. The values may be expressed as gags of hydroxyproline per mg of tissue and directly related to the collagen content.

Values may be expressed as mean+/−standard error of mean (SEM). The normality distribution of the data may be established using the Wilk-Shapiro test, and the outcome measures between two groups may be compared by the t-test according to the Graph Pad Prism Version 4.0 software package (GraphPad Software, San Diego, Calif.). Frequency histograms may be performed to compare the number of fiber versus fiber size and then analyzed by the Chi square test of goodness fit. Differences among groups may be considered significant at $p<0.05$.

5. Results

A. Silencing Myostatin Expression in Cell Culture Using a Short Interfering Hairpin RNA Targeting Myostatin (Mst-shRNA).

Figures 2A, 2B, 2C:
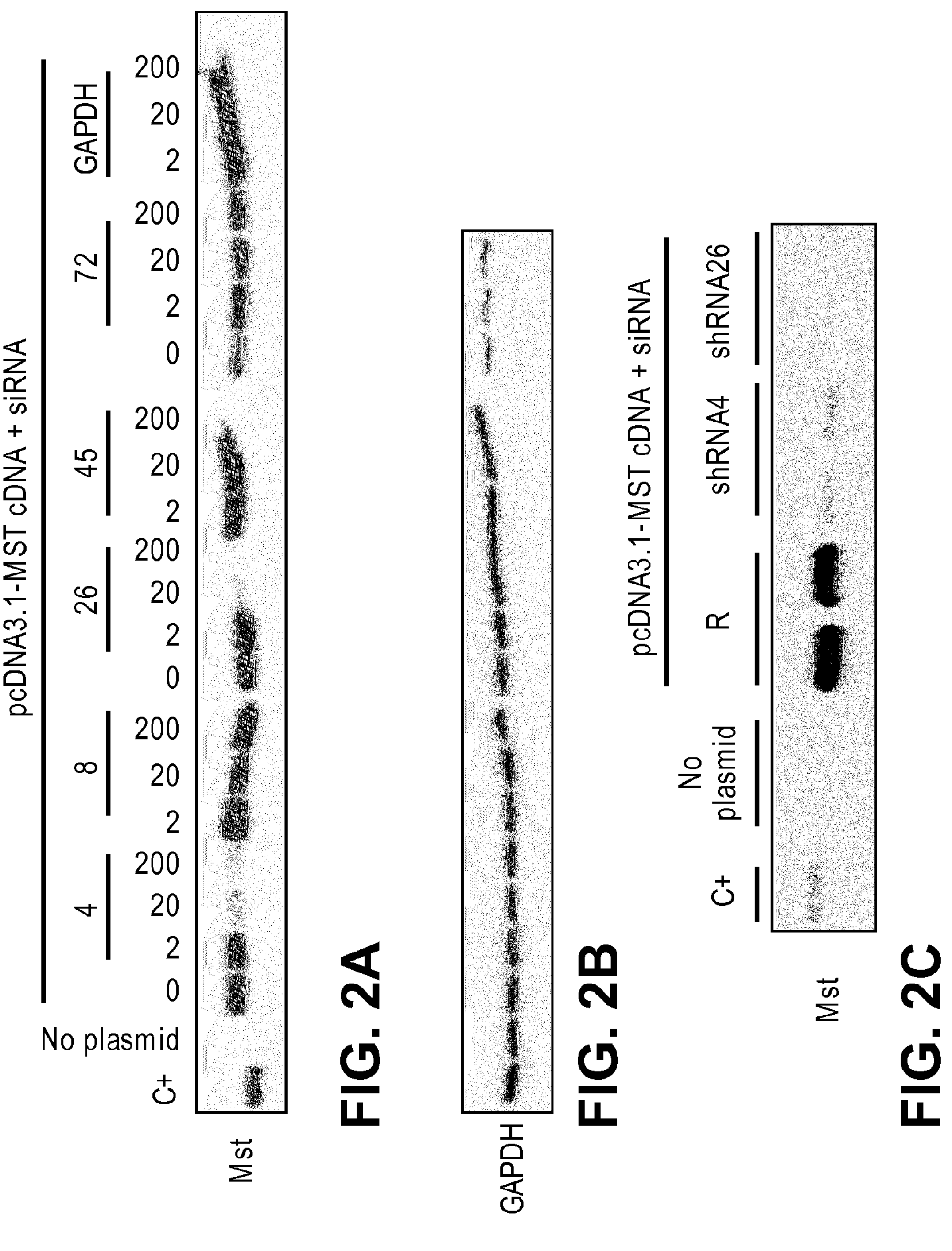
FIGS. 2A-C illustrate effects of myostatin short interfering RNA (siRNA) and short interfering hairpin RNA (shRNA) on myostatin protein expression in cell culture.

Following transfection of the HEK293 cells with the myostatin expressing plasmid, western blot analysis may be performed using an anti-myostatin antibody. FIG. 2A represents a western blot analysis of myostatin protein following co-transfection of a myostatin expressing plasmid and double-stranded siRNAs targeting myostatin wherein siRNA concentrations were 0, 2, 20, and 200 nM, C+ represents a mouse control skeletal muscle protein lysate and +plasmid is illustrated as pcDNA3.1-mouse myostatin. As illustrated in FIG. 2A, using the above procedures, two Mst-siRNAs (siRNA4 and siRNA26) that were over 80% effective at blocking the expression of the 50 kilodalton (kDa) myostatin band corresponding to the full length protein (375 amino acids) at a concentration of 20 nanometers (nM) were identified. SiRNA4 as referenced herein may be 5'-AAATGAGGGCAGTGAGAGAGA-3' (nucleotide position 175, SEQ ID NO: 10). FIG. 2B shows myostatin expression analysis repeated for siRNAs showing most effective silencing, and in particular, represents protein expression of the housekeeping protein glyceraldehyde-3-phosphate dehydrogenase (GAPDH) from lysates in the example illustrated in FIG. 2A. As illustrated in FIG. 2B, siRNA targeting GAPDH was not effective at 20 nM and only slightly inhibitory at 200 nM. It is believed that this may be due to non-specific transcriptional inhibition at such a high concentration. No inhibition of the housekeeping gene GAPDH was detected even at 200 nM in the cells that had been incubated with the Mst-siRNAs.

FIG. 2C shows results from the testing of short hairpin DNAs containing vectors representing the corresponding region for each siRNA. In FIG. 2C, C+ represents a mouse control skeletal muscle protein lysate, no plasmid represents untransfected cell cultures, R represents randomer shRNA (R-shRNA) a negative control cotranfected with myostatin expressing plasmid, shRNA represents short interfering hairpin RNAs targeting myostatin (Mst-shRNAs) cotransfected with myostatin expressing plasmid at a 1:1 ratio. In particular, it can be seen that following co-transfection of pcDNA3.1-mouse myostatin and each pSILENCER® plasmid (1:1 ratio; 1 μg each), the Mst-shRNA26 blocked virtually all expression of myostatin by western blot analysis. The myostatin shRNA4 construct may also block expression but to a lesser degree. These results were similar to the silencing seen using the corresponding double stranded siRNAs. A Blast sequence homology search of the mouse 21-mer Mst-siRNA26 showed the siRNA target to be highly conserved in mammals and was found to have 100% homology to human, rat, rabbit, cow, macaque, and baboon. All further experiments were done with the shRNA26 plasmid construct.

B. Down Regulation of Myostatin Gene Expression in the Tibialis Anterior Muscle and Increase of Myosin Heavy Chain II.

Figure 3A:
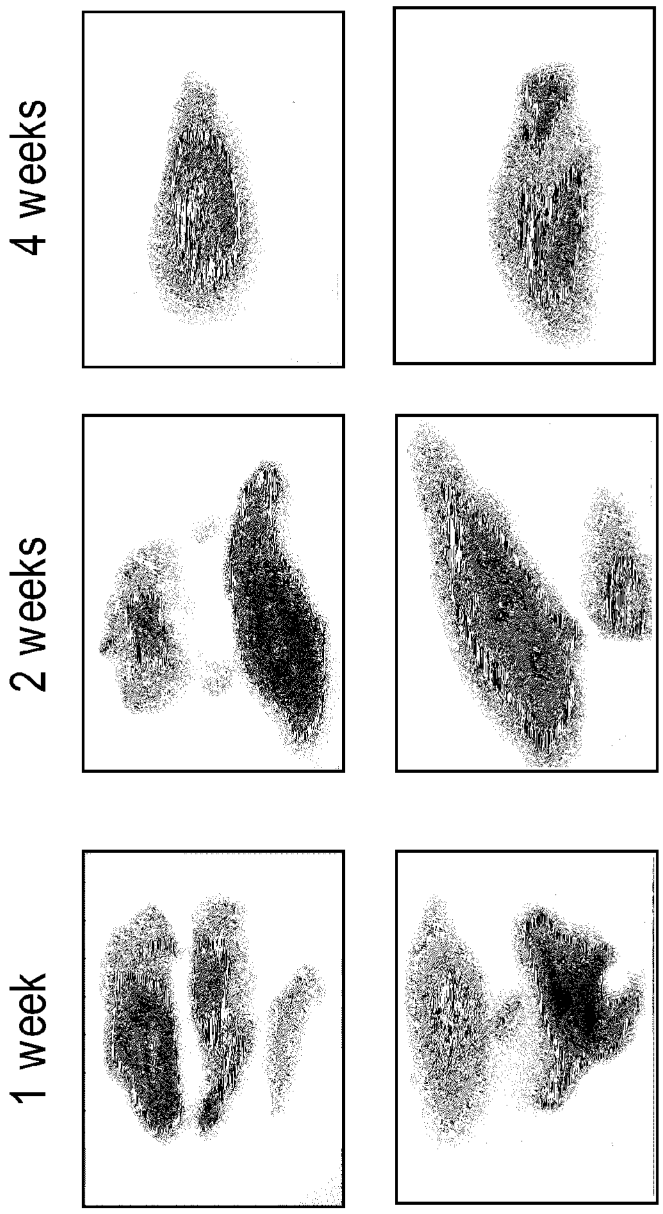
FIGS. 3A-B illustrate beta-galactosidase reporter expression in a tibialis anterior muscle.
Figure 3B:

It is believed that gene transfer to, for example, the skeletal muscle tissue is likely to be transient and centered around the site of injection. In order to assess the spread and persistence of a plasmid gene transfer throughout the tibialis anterior muscle, the expression of a plasmid expressing the beta-galactosidase reporter protein, under conditions identical to the ones used for the myostatin gene transfer may be examined. FIG. 3A represents frozen tissue blocks of tibialis anterior muscle for two rat samples following gene transfer at 1, 2 and 4 weeks having areas expressing beta-galactosidase. As illustrated in FIG. 3A staining for beta-galactosidase expression in frozen tissue blocks showed that the majority of the tibialis anterior muscle took up plasmid, but expression, as expected, was not evenly distributed across the tissue, with the majority of expression near the sites of injection and tapering off near the ends and the opposite side of the tissue. FIG. 3B illustrates representative longitudinal tissue sections at a higher magnification of 40× and wherein the bar equals 500 micrometers. Expression was relatively similar at one and two weeks and decreased approximately by half at four weeks.

After determining the uptake and persistence of a plasmid construct, 100 μg of a solution including the Mst-shRNA construct may be injected and electroporated under identical conditions into one tibialis anterior muscle or R-shRNA (negative control) to the contra lateral tibialis anterior muscle, and the animals sacrificed at two weeks only (n=9/group).

Figure 4:
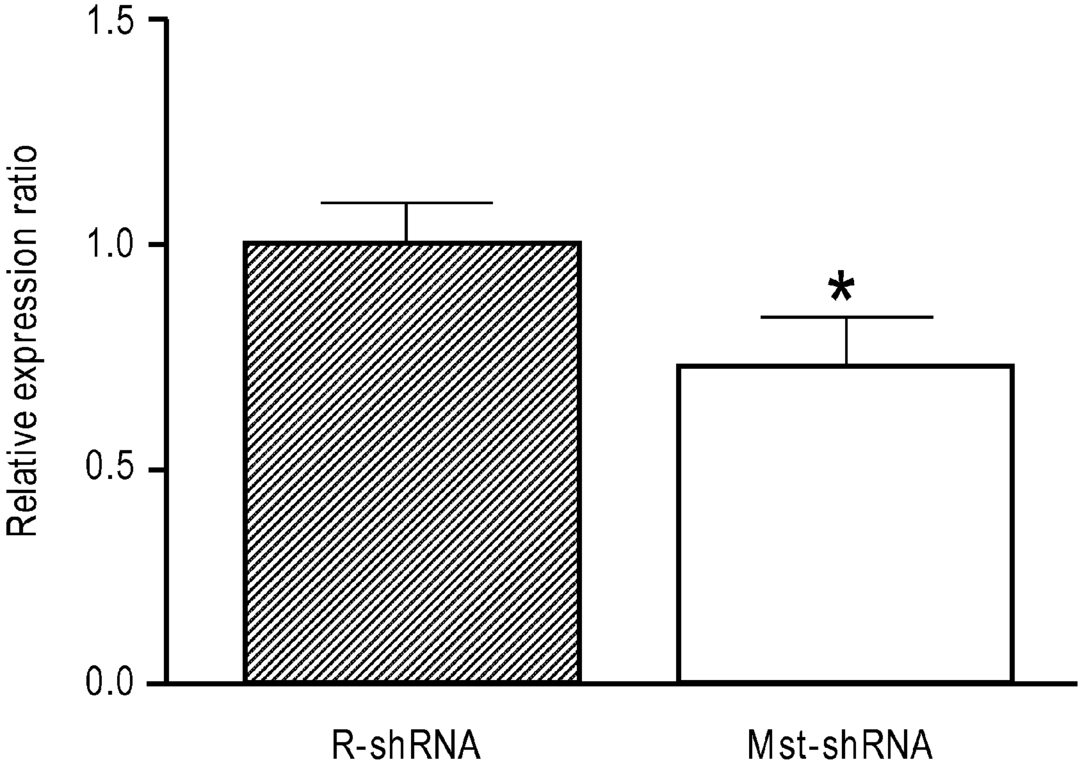
FIG. 4 illustrates results of a real time polymerase chain reaction (RT-PCR) of myostatin mRNA expression in R-shRNA (negative control) and Mst-shRNA treated samples.

FIG. 4 illustrates results of a real time polymerase chain reaction (RT-PCR) of myostatin mRNA expression in R-shRNA (negative control) and Mst-shRNA treated samples (n=9 per group) under these conditions. Myostatin expression was normalized to GAPDH expression and denoted as a myostatin/GAPDH ratio (*$p<0.05$). As illustrated in FIG. 4, under these conditions, myostatin mRNA expression, as determined by real-time RT-PCR in RNA isolated from tissue aliquots from the same locations in the tibialis anterior, and corrected for expression of the housekeeping gene GAPDH, decreased significantly by 26.7% in Mst-shRNA treated muscle compared to the R-Mst-shRNA treated (negative control), contra lateral muscle in each animal.

Figure 5A:
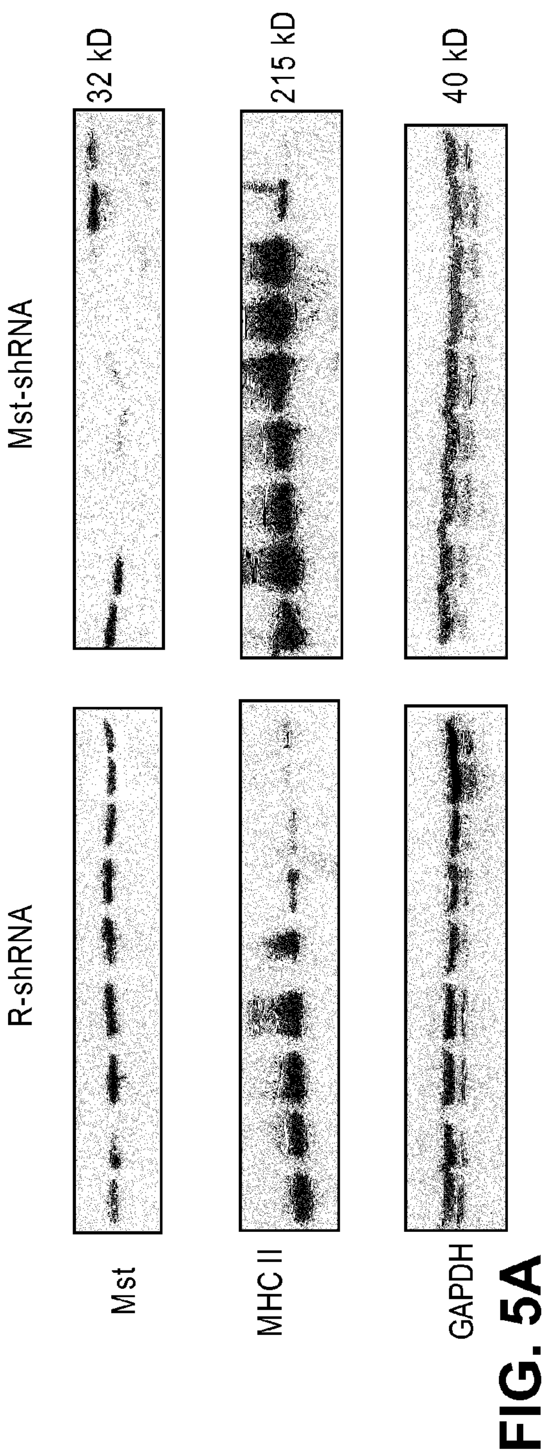
FIGS. 5A-C illustrate expression of myostatin and myosin heavy chain type II (MHCII) following shRNA gene transfer.
Figure 5B:
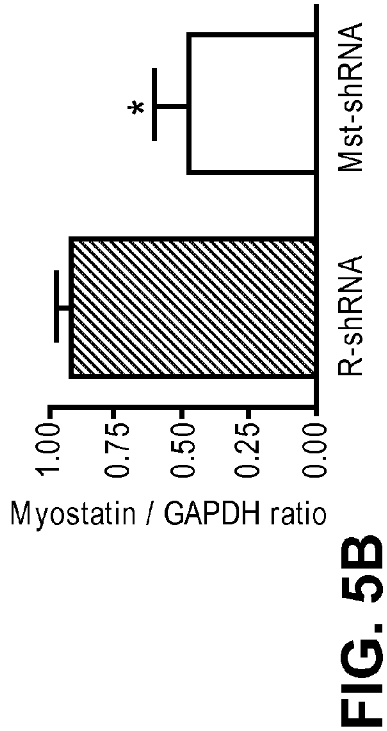
Figure 5C:
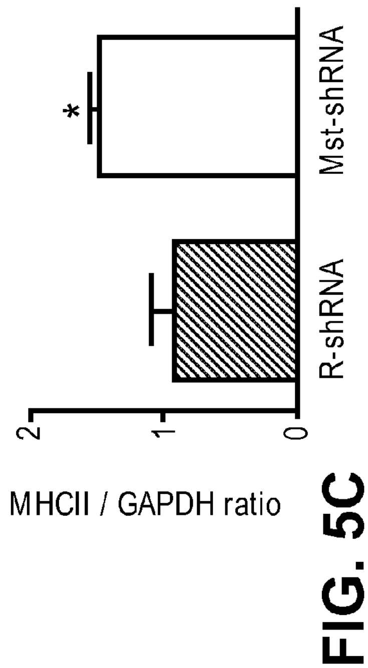

FIGS. 5A-C illustrate expression of myostatin and myosin heavy chain type II (MHCII) following shRNA gene transfer, (9 tissue lysates from each treatment group). FIGS. 5A-B further confirm the presence of myostatin silencing, by showing myostatin protein levels significantly decreased (i.e. by 48.3%) in the Mst-shRNA treated rats as compared to R-shRNA-treated muscles. In particular, FIG. 5A represents western blotting of myostatin, MHCII, and GAPDH in rat muscle tissue extracts wherein the left panel illustrates randomer negative control treated tissue lysates and the right panel illustrates myostatin shRNA treated tissue lysates. FIG. 5B represents a densitometric analysis of the myostatin/GAPDH ratio expression determined by western blot analysis (*$p<0.05$). In view of these results, it is believed that down-regulation of myostatin expression should activate myofiber growth, which should be reflected by an increase in muscle specific gene expression. Such an occurrence is supported by the results illustrated in FIG. 5C. FIG. 5C represents a densitometric analysis of the MHCII/GAPDH ratio expression determined by western blot analysis (*$p<0.05$). FIG. 5C shows that myosin heavy chain type II, one of the main contractile proteins, and a marker of fast myofibers, was found by western blot to increase significantly by 37.8% in Mst-shRNA treated tibialis anterior tissue, as compared to the contra lateral muscle injected with R-shRNA.

C. Tibialis Anterior Muscle Mass Increases Following Myostatin Down-Regulation.

Initially, it may be observed that during dissection of the tissue that Mst-shRNA treated, tibialis anterior muscle is noticeably larger in some of the animals as compared to R-shRNA injected muscle tissue. These observations are illustrated in the results shown in FIGS. 6A-D. FIG. 6B represents the weight (milligrams or mgs) of a whole tibialis anterior muscle from both treatment groups (*$p<0.05$). In particular, as illustrated in FIG. 6B weighing of each muscle reveals a statistically significant increase in overall muscle weight in the Mst-shRNA-treated muscles of 9.8% over the R-shRNA-treated contra lateral muscles. A portion of each muscle, adjacent to the one used for RNA isolation and protein analysis by western blot, may be fixed in formalin, paraffin embedded, and examined for muscle fiber size.

Figure 6A:
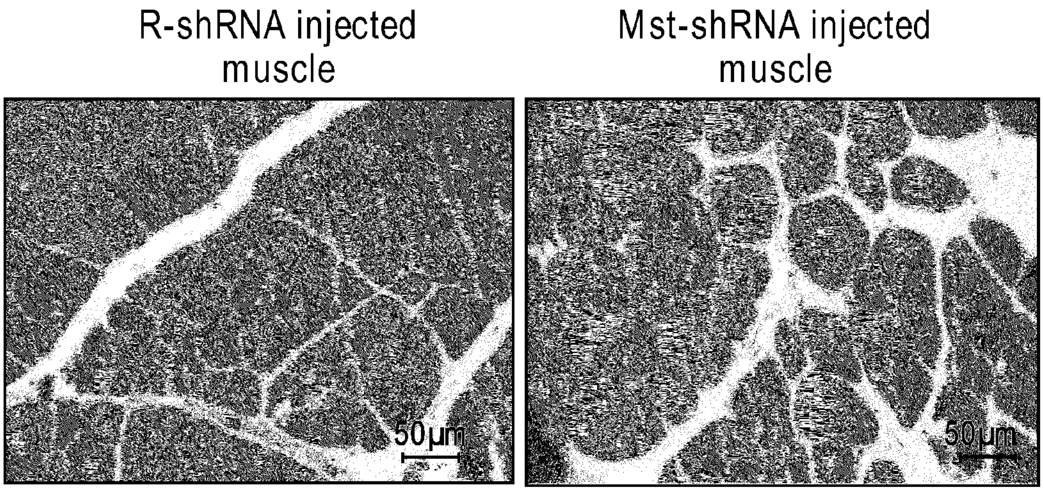
FIGS. 6A-D illustrate muscle fiber size and morphology following shRNA gene transfer.
Figure 6B:
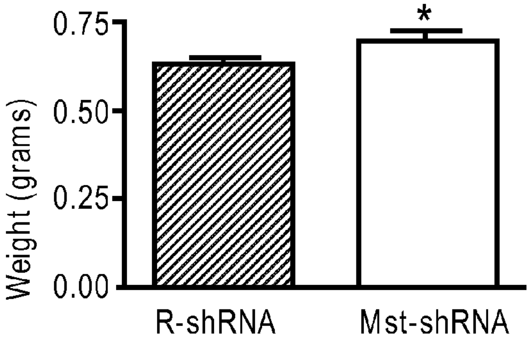

FIG. 6A shows the differences in myofiber sizes. In particular, FIG. 6A shows representative micrographs of tibialis anterior muscle treated with a R-shRNA plasmid construct (left) and Mst-shRNA plasmid construct (right) wherein magnification is 200× and the bar equals 50 micrometers. Representative micrographs of paraffin-embedded cross-sections of the Mst-shRNA-treated tibialis anterior as compared to the R-shRNA-treated contra lateral muscle in FIG. 6A shows that the myofibers are visibly larger in the former. The sizes of approximately 100 myofibers may be examined per muscle the results of which are illustrated in FIG. 6C.

Figure 6C:
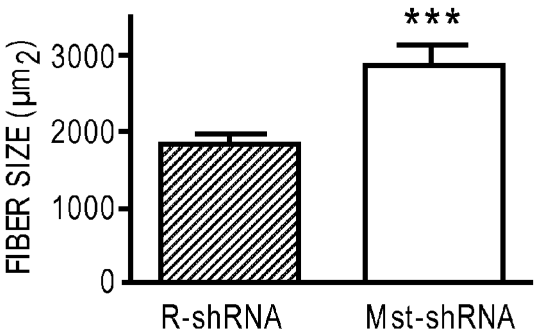

FIG. 6C represents a muscle fiber area determined by quantitative image analysis of 100 fibers per sample, 9 samples per group (***$p<0.01$). Overall, Mst-shRNA muscle fiber area was increased 34.2% as compared to the R-shRNA control muscle fiber area. Examining the population of myofiber sizes indicates a shift from smaller fibers to larger fibers in the Mst-shRNA treated tissue. In particular, the interstitial connective tissue is significantly reduced by 39.7% (2746+/−152

$microm^2$ in Mst-shRNA versus 1656+/−82 $microm^2$ R-shRNA). This, however, was not reflected in a change in the levels of collagen, as estimated by hydroxyproline (12.84+/−1.41 mg/mg tissue homogenate in Mst-shRNA vs 12.96+/−2.4 mg/mg tissue homogenate R-shRNA).

Figure 6D:
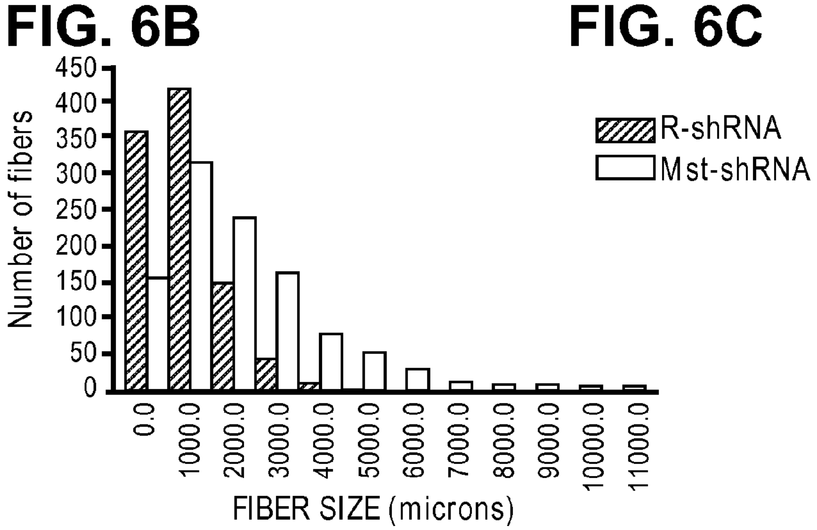

FIG. 6D represents the number of fibers versus fiber size plotted in a frequency histogram for R-shRNA (black columns) and Mst-shRNA (white columns) wherein Mst-ShRNA produced a significant right shift of the histogram to larger fiber size, $\chi^2$ df: 299.8; ***p<0.01.

D. Increase in Muscle Mass and Fiber Size by Mst-shRNA Gene Transfer is Paralleled by an Increase in the Number of Satellite Cells.

In order to gain insight into whether the muscle hypertrophy induced by myostatin silencing observed above is accompanied by replication of satellite cells that would eventually fuse their nuclei with the existing myofibers, a determination of satellite cell number increase in the Mst-shRNA treated tissue must be made. In one embodiment, the tibialis anterior tissue sections for paired box gene 7 (PAX7), a specific marker of satellite cells, may be immuno-stained and examined. The results upon examination of these tissue sections are illustrated in FIGS. 7A-B.

Figure 7A:
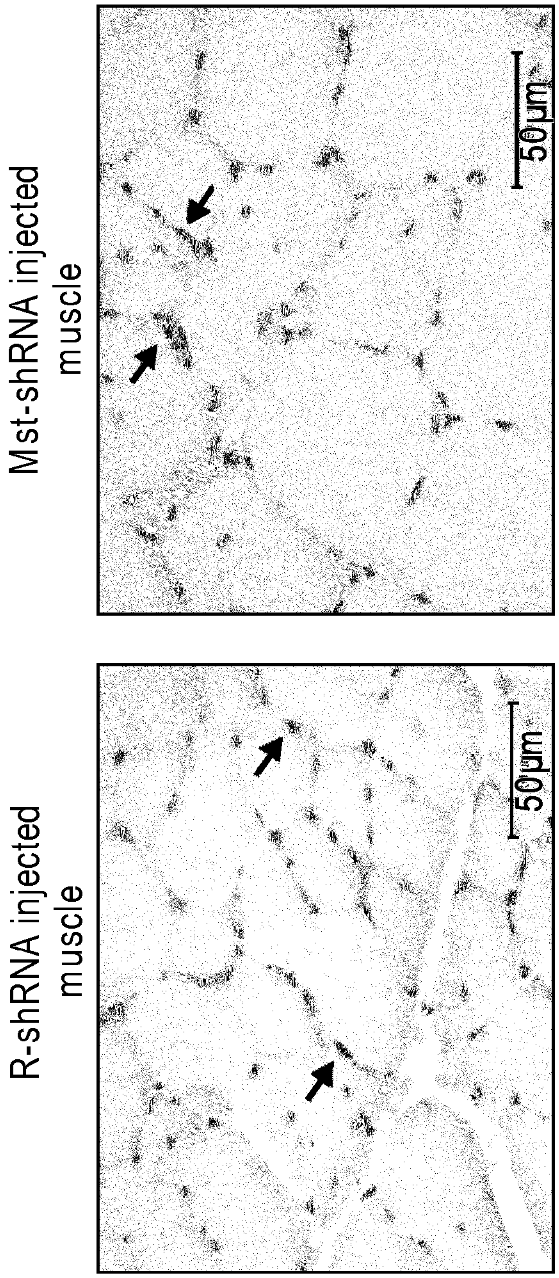
FIGS. 7A-B illustrate paired box gene 7 (PAX7) expression.
Figure 7B:
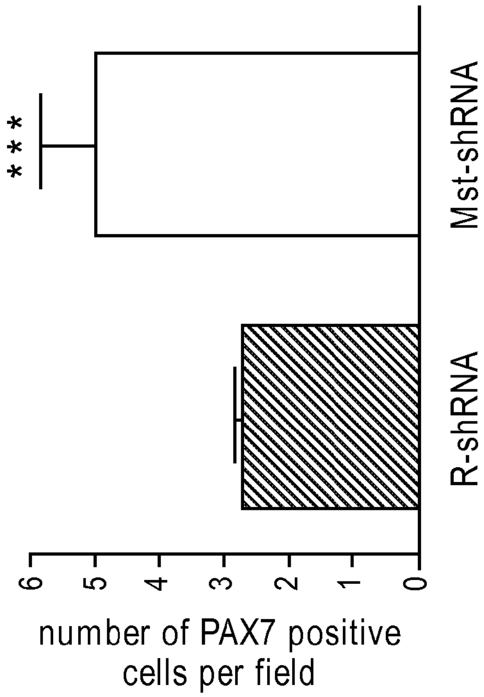

FIG. 7A shows representative micrographs of satellite cells expressing PAX7 immunostained (darkened regions) and denoted with arrows at a magnification of 400× having a bar equal to 50 micrometers. FIG. 7B represents a densitometric analysis of the PAX7 immunostained positive cells (darkened regions) per field at 10 fields per sample (*p<0.01). As illustrated in FIG. 7A upon examination, an increased number of PAX7 positive cells (darkened regions indicated by arrows) in the Mst-shRNA muscle may be observed. By applying quantitative image analysis, the number of satellite cells per field staining for PAX7 may be determined. In particular, it is observed that the number of satellite cells per field increased by 64.3% with Mst-shRNA treatment as compared to the R-shRNA, suggesting that at least part of the muscle increase is related to satellite cell activation (see FIG. 7**B).

Example II

1. Myostatin is a Growth Inhibitor and Pro-Fibrotic Factor in the Smooth Muscle, and Counteracting it Stimulates Smooth Muscle Proliferation Thus Increasing Penile Size and Preventing Fibrosis.

Although myostatin has been previously shown to be expressed in skeletal muscle tissue, embodiments and results which will now be described are the first to demonstrate that myostatin is also expressed in smooth muscle, specifically in the penile corpora cavernosa. In particular, myostatin expression may be found in both the corpora cavernosa (primarily smooth muscle) and in the tunica albuginea (primarily fibroblasts and myofibroblasts).

Since myostatin inhibits cell growth and we have found that it is expressed in smooth muscle cells, this suggests that it acts as a smooth muscle cell growth inhibitor, that is blocking cell replication. Considering that smooth muscle is the bulk of the penile shaft, we believe that blocking myostatin expression and/or activity will increase penile corpora cavernosa size, that is penile size. To prove this inhibition of myostatin in the penis by the shMst RNA and the resulting effect on penile size is examined.

A. Expression of Myostatin in Penile Smooth Muscle Cells and Fibroblasts.

Figure 8C:
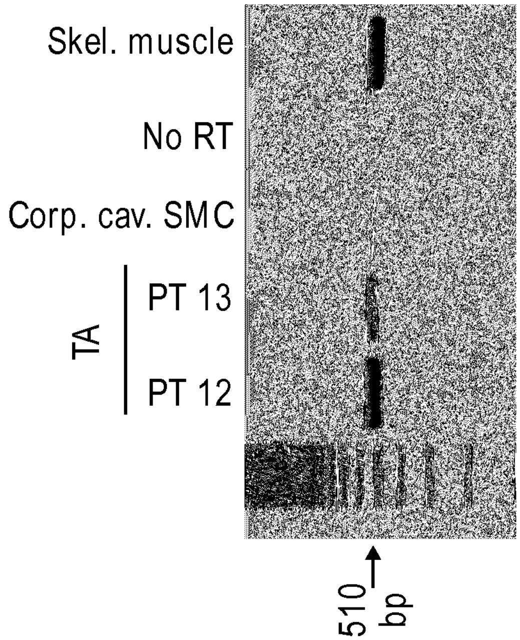
FIGS. 8A-C illustrate myostatin expression in penile smooth muscle cells.
Figure 8A:
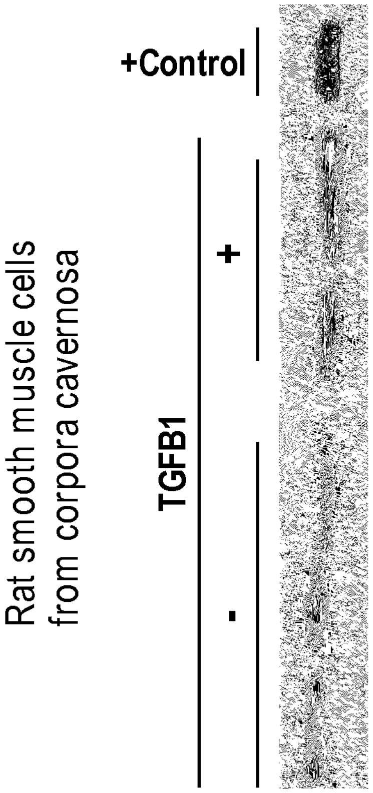
Figure 8B:
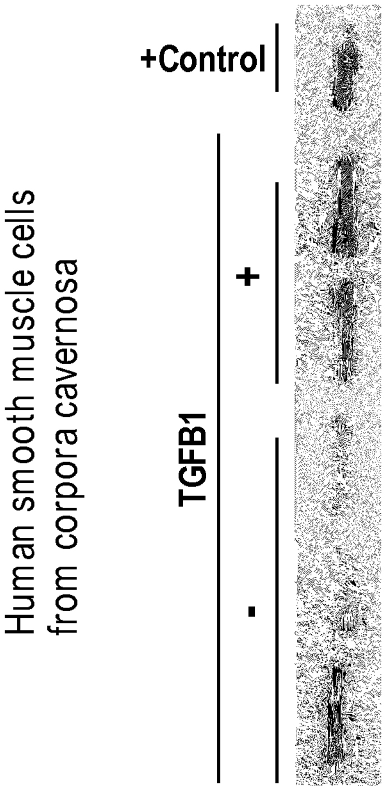

FIGS. 8A-C illustrate myostatin expression in smooth muscle cells, and in particular, penile smooth muscle cells. FIGS. 8A-C show detection of myostatin by two different procedures in smooth muscle cell cultures obtained from human corpora cavernosa biopsies and rat penile tissue. Such expression has further been shown in cultures from tissue pieces dissected from the normal human and rat penile tunica albuginea that in vitro contain primarily fibroblasts. These fibroblasts can undergo differentiation into myofibroblasts both in vivo and in vitro and thus induce fibrosis. Cells from both cultures may be lysed and processed for extracting RNA and protein similar to the manner done for skeletal muscle. In particular, FIG. 8A shows myostatin expression from smooth muscle cells derived from a rat. FIG. 8B shows myostatin expression from smooth muscle cells derived from a human penis. FIG. 8C shows results wherein the cells were lysed for RNA extraction. The extracted RNA was then reverse transcribed and subjected to RT-PCR, run on an agarose gel, stained with ethidium bromide and then photographed. The Western blot and RT/PCR results illustrated were then confirmed by immunohistochemistry and immunocytochemistry with the antibody against myostatin.

FIGS. 8A-B shows that in two separate incubations of rat or human penile cells, conducted in triplicate or duplicate wells, myostatin is expressed in the smooth muscle cells derived from the corpora cavernosa of the penis and that myostatin expression is increased by incubation with a pro-fibrotic factor TGFbeta1. This was confirmed in FIG. 8C by RT/PCR on RNA extracted from these cells, as well as from human tunica albuginea fibroblasts, showing a 510 bp DNA band corresponding to amplified DNA from the myostatin mRNA.

In FIG. 8A rat smooth muscle cells grown from tissue explants in cell culture are treated for 2 days with or without TGFbeta1 protein (5 ng/ul), which is a well known pro-fibrotic factor. The cells were then lysed and processed for western blotting with an anti-myostatin antibody and luminol detection on X-ray films. FIG. 8B illustrates human smooth muscle cells treated similarly as in panel FIG. 8A. In FIG. 8C cells were lysed for RNA extraction as previously done for skeletal muscle cells. RNA was reverse transcribed and subjected to RT-PCR, run on an agarose gel, stained with ethidium bromide and photographed. As used in FIG. 8C, "TA" represents Tunical albuginea fibroblast cultures, "Corpora. cay. SMC" represents smooth muscle cells from the corpora cavernosa of the penis, "No RT" represents negative control reaction and "Skel. muscle" represents Human skeletal muscle positive control.

B. Expression of Myostatin in Smooth Muscle and Tunica.

Figure 12A:
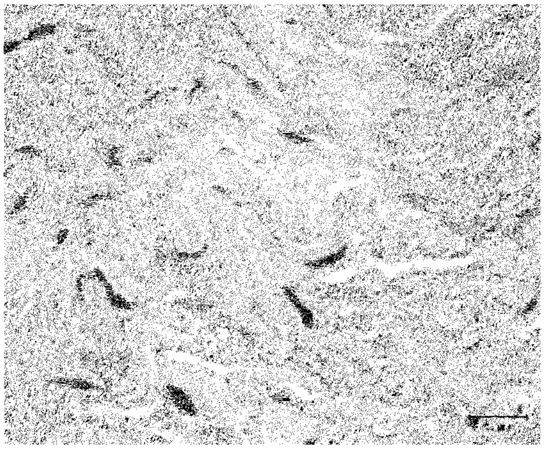
FIGS. 12A-C illustrate expression of myostatin in human tissue sections of tunica albuginea of a control patient and a patient with Peyronie's disease.
Figure 12B:
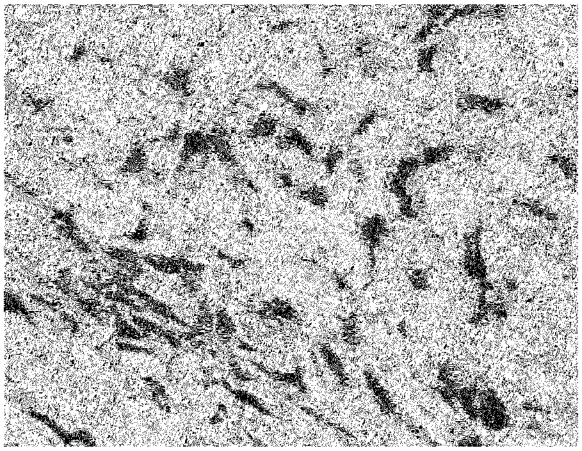
Figure 12C:
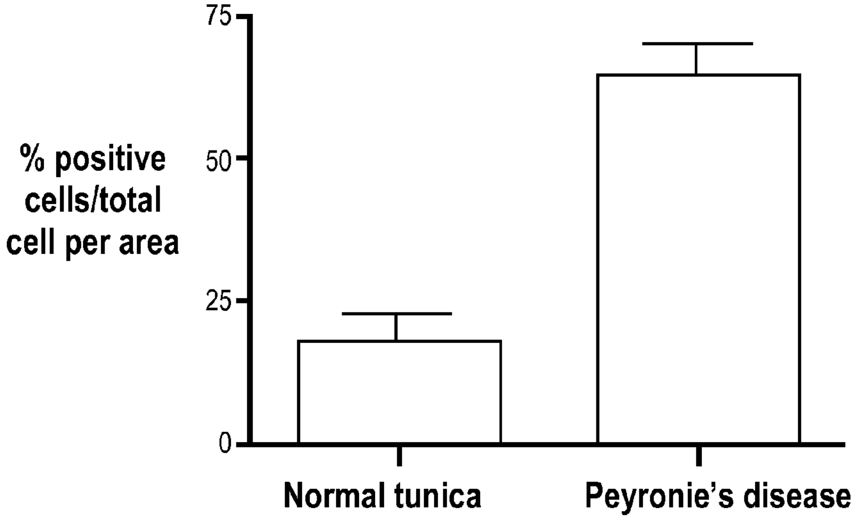

FIG. 12 illustrates expression of myostatin in human tissue sections of tunica albuginea of a control patient and a patient with a fibrotic condition named Peyronie's disease. Myostatin is highly expressed in Peyronie's disease patients that have palpable plaque in the tunica. In this embodiment, paraffin embedded sections were stained with a polyclonal antibody against myostatin (custom made) and counterstained with hematoxylin. Cross-sections of the human penile shaft as illustrated in FIGS. 12A-B clearly show myostatin staining in fibroblasts of the normal tunica albuginea (FIG. 12) and this is notably intensified in the fibrotic plaque of the tunica albuginea named "Peyronie's disease" (FIG. 12B). These results are confirmed by quantitative image analysis as illustrated in FIG. 12C.

Figure 13A:
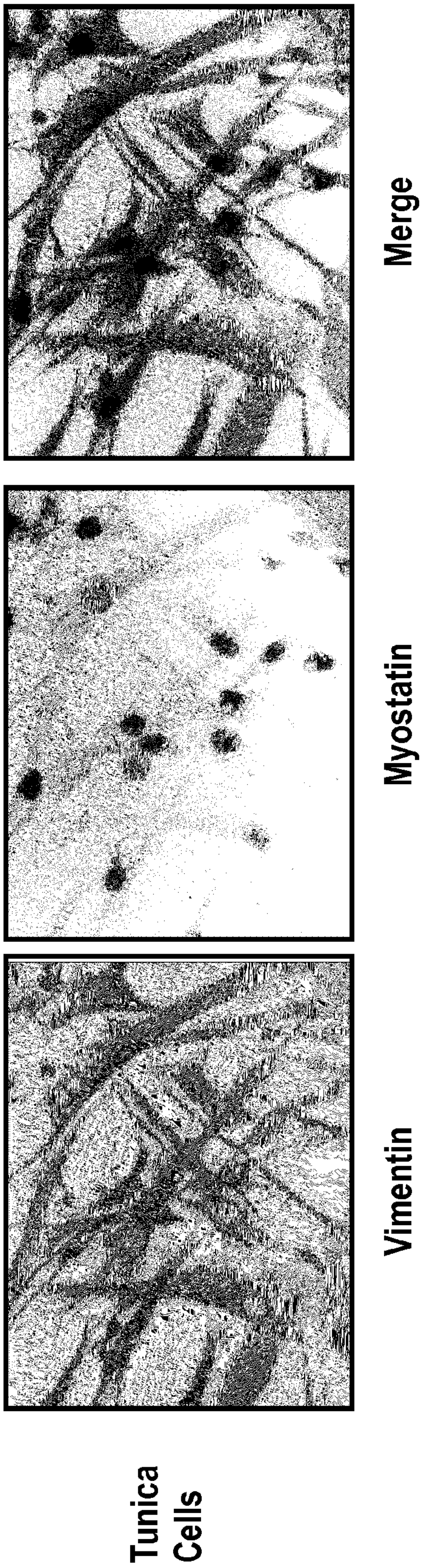
FIGS. 13A-B illustrate expression of myostatin in human fibroblasts from a control patient and a Peyonie's disease patient.
Figure 13B:
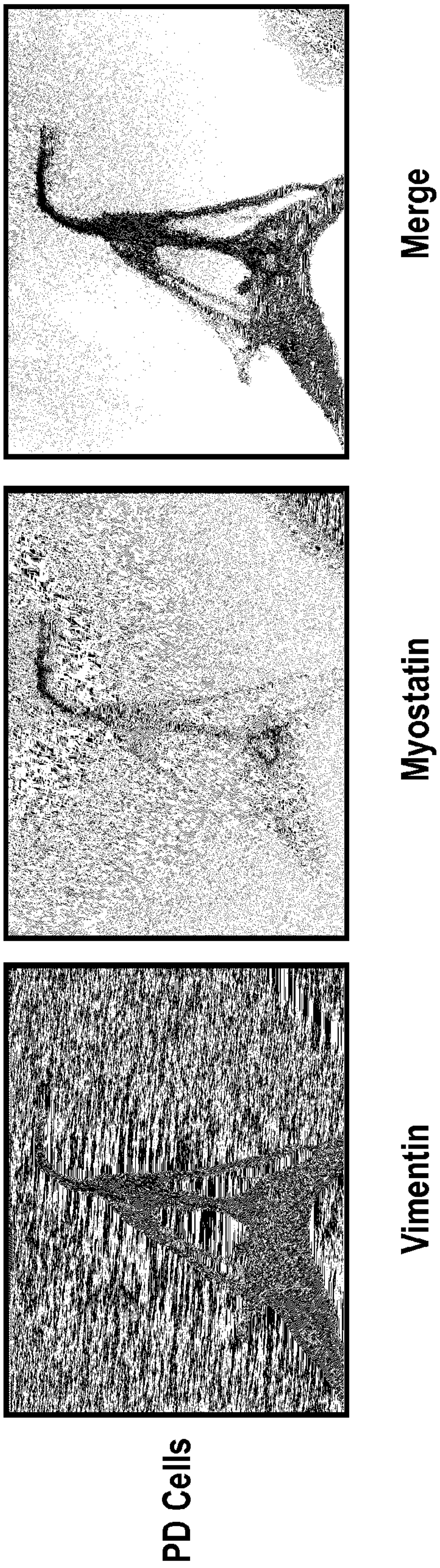

Still further, the resulting expression of myostatin in tunica albuginea myofibroblasts (fibrotic cells) is confirmed by dual confocal microscopy in FIGS. 13A-B. In particular, FIG. 13A illustrates expression of myostatin in human fibroblasts from a control patient while FIG. 13B illustrates myostatin expression from a Peyonie's disease patient. Myostatin expression in cell culture is localized in the nucleus of the cells and may therefore be visualized as shown in FIGS. 13A-B. In particular, biopsies from both patients were trypsinized and the cells were cultured in a fibroblast growth media. After several passages, the cells were plated in a 8 slides chamber slides and dual colocalization with a vimentin antibody (fibroblast marker) and myostatin antibody. Myostatin expression in cell culture is localizaed in the nucleus of the cells, presumably because it acts as a transcription factor.

For both FIG. 13A and FIG. 13B, the left panel shows the expression of vimentin (a marker of fibroblast cells) localized in the cytoplasm of tunica and PD cells (light gray color in the cytoplasm), whereas the middle panel shows the expression of myostatin in the nucleus of these cells (dark gray-black staining in the nucleus). The right panel shows the merge of both images showing a perfect localization of myostatin in the nucleus with a localization of the vimentin in the cytoplasm. This finding shows that myostatin is expressed in fibroblast cells, because of the co-localization of the fibroblast marker with the expression of myostatin in the nucleus.

Figure 14A:
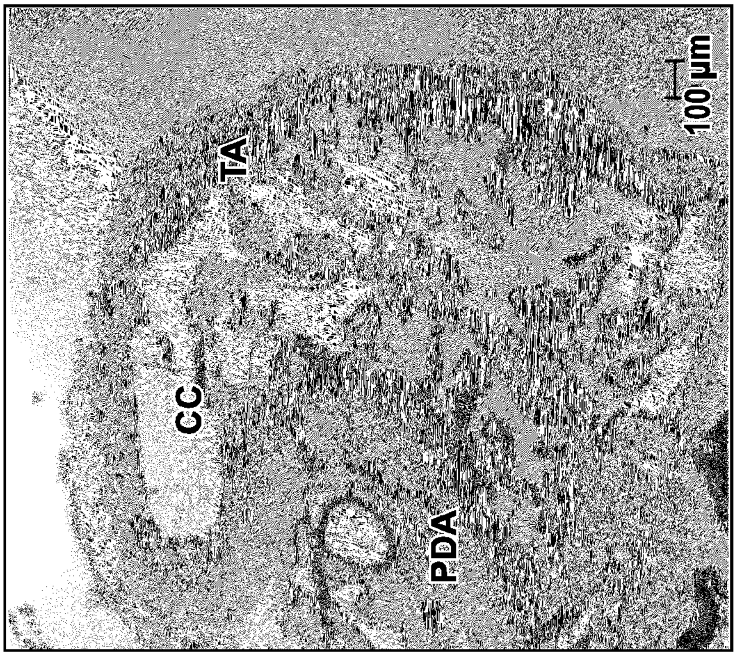
FIGS. 14A-B illustrate expression of myostatin in the rat penis.
Figure 14B:
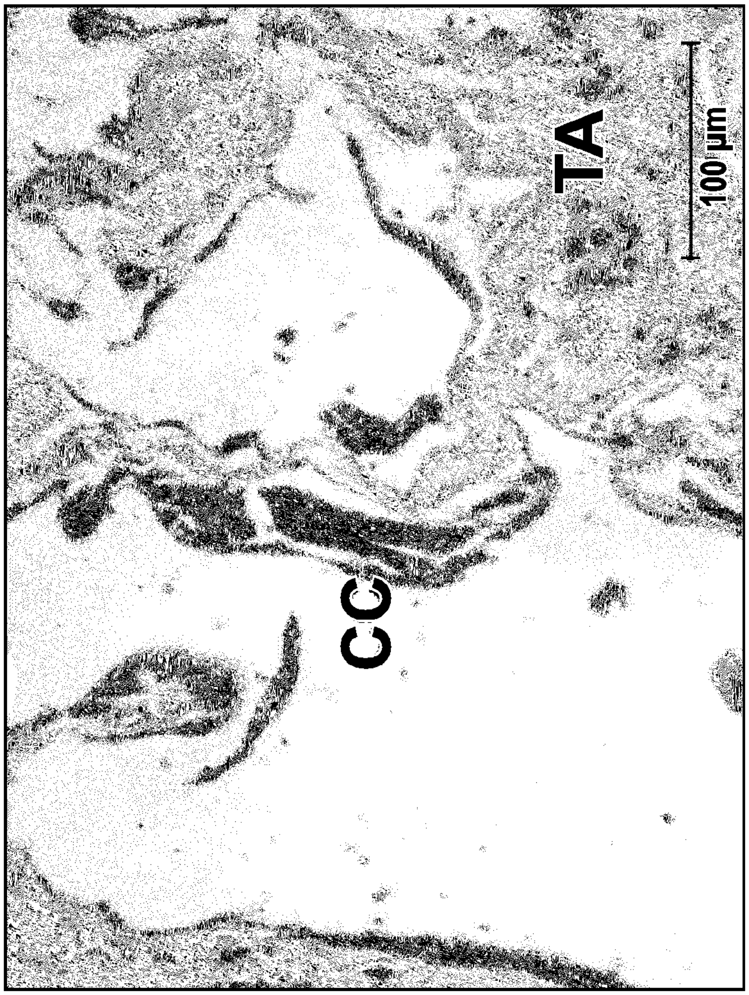

FIGS. 14A-B illustrate expression of myostatin in the rat penis at low and high magnifications. In particular, paraffin embedded sections were stained with an antibody against myostatin and counterstained with hematoxylin. Immunocytochemical detection of cross-sections of the rat penis allows for precise localization of myostatin in the trabecular smooth muscle around the cisternae, as shown in FIGS. 14A-B. Myostatin is expressed in the media of the penile dorsal artery (PDA), in the corpora cavernosa (CC) and in the tunica albuginea (TA)

Figure 15A:
FIGS. 15A-B illustrate expression of myostatin in the smooth muscle cells of the corpora cavernosa and dorsal artery of the penis.
Figure 15B:
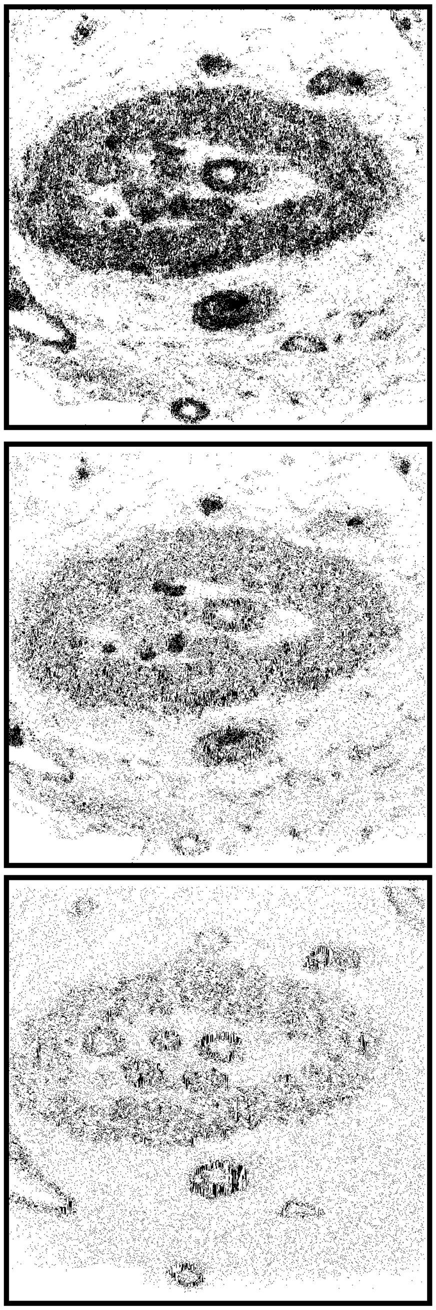

FIGS. 15A-B illustrate expression of myostatin in the smooth muscle cells of the corpora cavernosa (FIG. 15A) and dorsal artery (FIG. 15B) of the penis of the tissue sections illustrated in FIGS. 14A-B. Rat tissue sections were incubated with antibodies against alpha smooth muscle actin (ASMA or α-SMA) (marker of smooth muscle cells, red staining) and myostatin in a dual localization experiment. Dual immunohistochemistry in vivo on these sections, confirmed the colocalization of ASMA, a myofibroblast/smooth muscle cell marker (in this case in SMC based on their lining of the corporal cisternae) and myostatin. The co-localization of ASMA and myostatin are shown by the darkened portions of the merge pictures of FIGS. 15A and 15B.

In particular, a left panel of FIG. 15A shows the expression of ASMA in the corpora cavernosa (light gray staining). Middle panel shows the localization of myostatin (dark gray staining) in the same area and in the same cells. The right panel shows the merge of both images showing very intense dark gray-black staining. This result confirmed the colocalization of a myofibroblast/smooth muscle cell marker (in this case in SMC based on their lining of the corporal cisternae) and myostatin. A left panel of FIG. 15B shows the expression of ASMA in the media of the penile dorsal artery (light gray staining). The middle panel shows the localization of myostatin (gray staining) in the same media of the penile dorsal area. The right panel shows the merge of both images showing very intense dark gray-black staining. This result confirmed the colocalization of a smooth muscle cell marker and myostatin.

C. Inhibition of Myostatin in the Penis by the shMst RNA and Effect on Penile Size.

Figure 9:
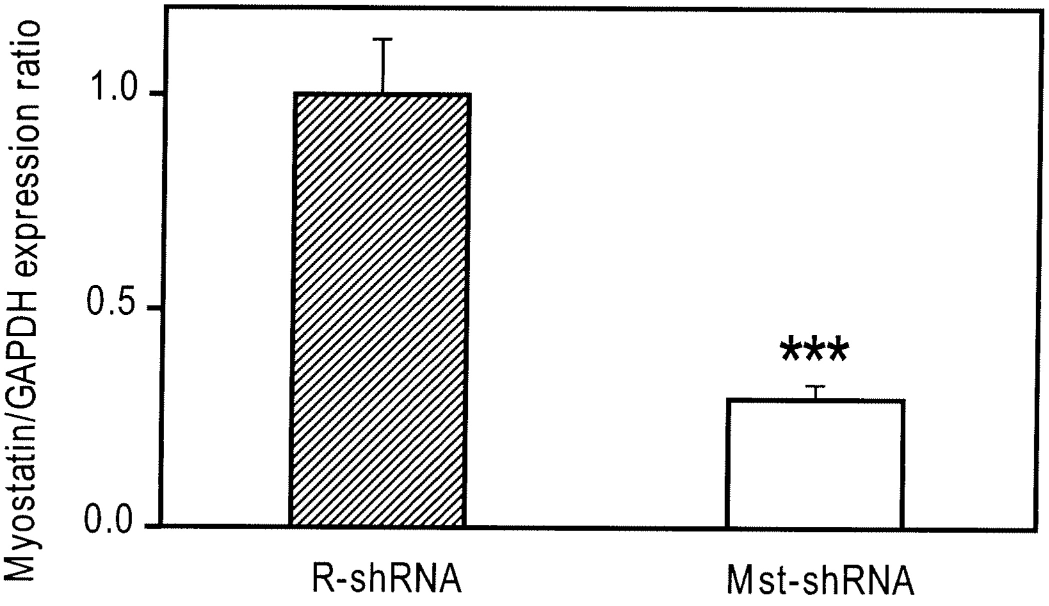
FIG. 9 illustrates myostatin mRNA expression in penile smooth muscle.

FIG. 9 illustrates myostatin mRNA expression in penile smooth muscle. In particular, a reduction in myostatin mRNA expression in Mst-shRNA treated smooth muscle samples as compared to R-shRNA treated samples is shown. In this aspect, a rat penis may be injected with 100 μg of either the pSILENCER® 2.1-U6 neo-myostatin siRNA plasmid construct or pSILENCER® 2.1-U6 neo-randomer plasmid and electroporated in a manner identical to that done for skeletal muscle (n=3 per group). After two weeks, smooth muscle tissue may be harvested and RNA from the penile smooth muscle tissue may be isolated. The RNA may be reverse transcribed and subjected to RT-PCR as was done for the skeletal muscle. Myostatin expression may be normalized to GAPDH expression and denoted as a myostatin/GAPDH ratio (*$p<0.001$). As can be seen from FIG. 9**, myostatin mRNA expression is reduced in the penile smooth muscle of the Mst-shRNA by 70.0% as compared to the R-shRNA control penile smooth muscle.

Figure 10:
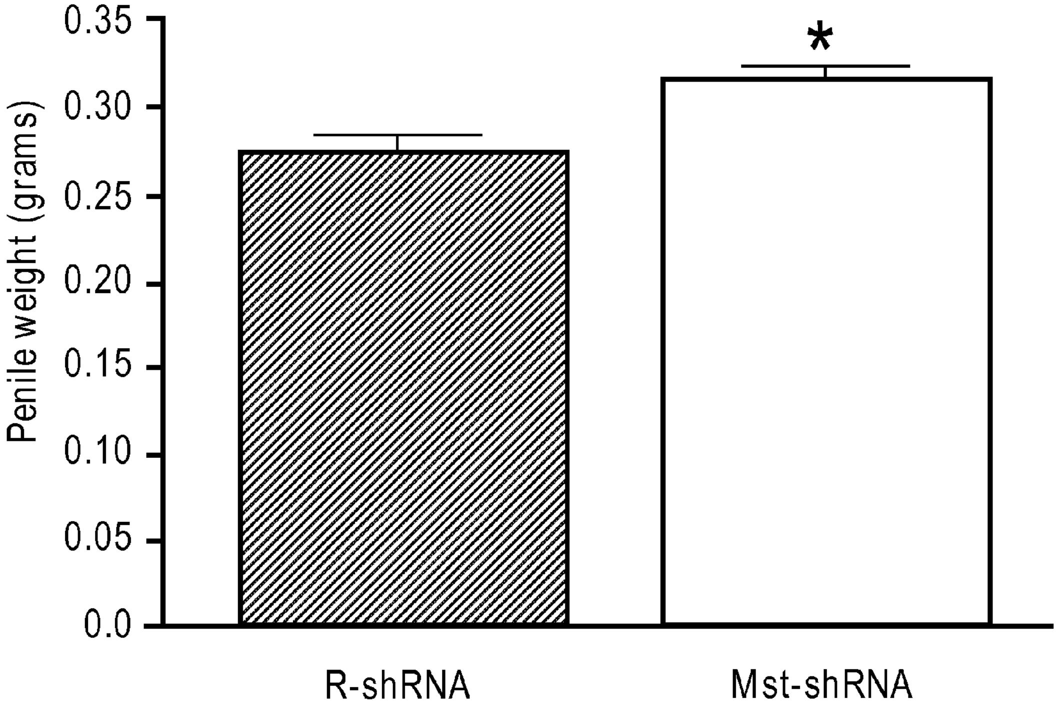
FIG. 10 illustrates average penile weight for R-shRNA and Mst-shRNA treated samples (*$p<0.05$).

FIG. 10 illustrates average penile weight for R-shRNA and Mst-shRNA treated samples (*$p<0.05$). In this aspect, increase in penile weight is correlated with injection of myostatin shRNA plasmid. Rat penis may be injected with 100 μg of either the pSILENCER® 2.1-U6 neo-myostatin siRNA plasmid construct or pSILENCER® 2.1-U6 neo-randomer plasmid and electroporated in a manner identical to that done for skeletal muscle (n=2, R-shRNA group; n=3, Mst-shRNA group) as previously discussed. After two weeks, the penises may be harvested and weighed. As shown in FIG. 10, penile weight increases on average by 16.8% in Mst-shRNA treated penises as compared to R-shRNA treated penises.

Figure 11A:
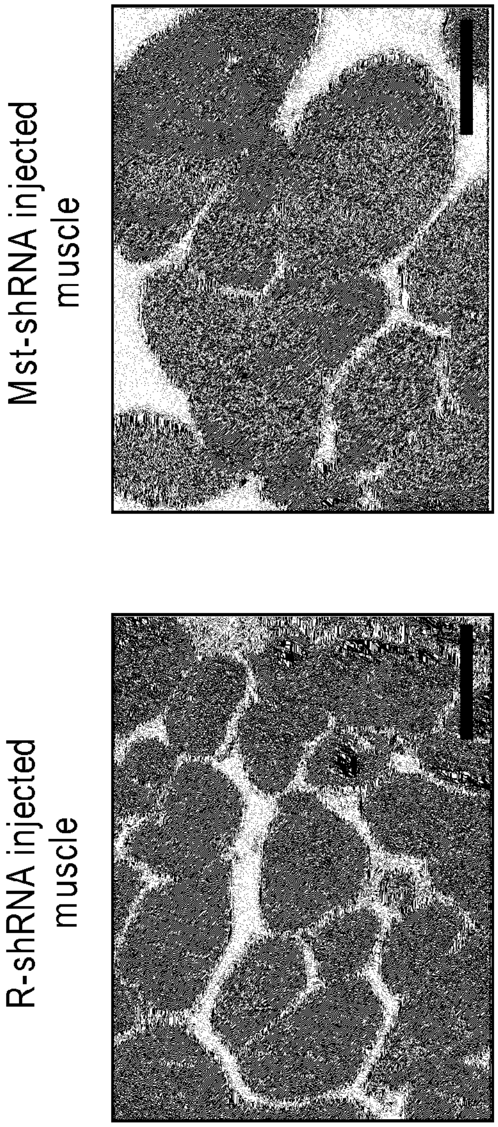
FIGS. 11A-B illustrate micrographs of interstitial connective tissue and an associated densitometric analysis graph.
Figure 11B:
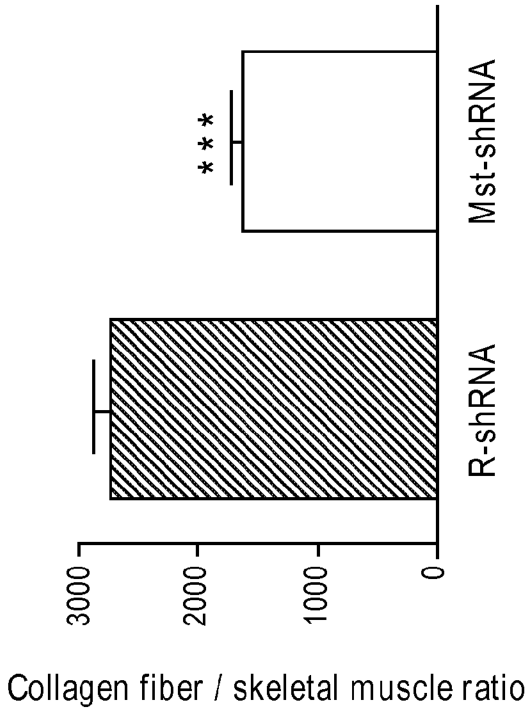

Moreover, as previously discussed, interstitial connective tissue may be attenuated by myostatin down-regulation by Mst-shRNA in post-natal normal animals, and potentially be an approach to reduce fibrosis in muscle dystrophies. FIGS. 11A-B illustrate a comparison of collagen fiber content for Mst-shRNA treated muscles and R-shRNA control tissue intra-muscular collagen. In particular, intramuscular collagen may be measured by Masson staining, as a marker of fibrosis to examine whether myostatin down-regulation is also associated with a reduction of interstitial connective tissue in the muscle of normal adult rats not subjected to injury. As illustrated in FIG. 11A, the content of collagen fibers decreases in representative micrographs in the Mst-shRNA treated muscles as compared to R-shRNA control tissue. The quantitative image analysis expressed as collagen per myofiber area per field illustrated in FIG. 11B shows that this ratio may be significantly decreased by as much as 39.7% by Mst-shRNA treatment.

The combined in vitro and in vivo results shown above indicate that myostatin is expressed in smooth muscle cells, and it is therefore believed that blocking myostatin may increase penile size such as by an increase in smooth muscle cell proliferation. Such results would have a variety of applications, including for example, penile compliance, e.g., rigidity during erection may be increased too. Moreover myostatin expression in the penile tunical fibroblasts intensifies in a fibrotic process of the tunica, Peyronie's disease, and that it is expressed in the cells responsible for the fibrotic process: the myofibroblasts.

Figure 16A:
FIGS. 16A-B illustrate human tunica albuginea cultures containing stem cells differentiating into myofibroblasts upon infection with AdV-MstcDNA.
Figure 16B:
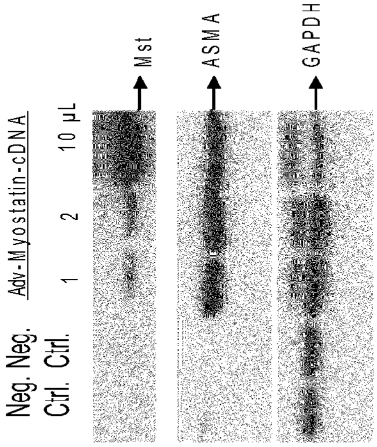

In view of the results discussed above, myostatin as a profibrotic factor may be tested by transfecting the human tunical cells previously discussed, with an adenoviral cDNA construct that we prepared that drives the expression of myostatin. FIGS. 16A-B illustrates human tunica albuginea cultures containing stem cells, differentiate into myofibroblasts upon infection with AdV-MstcDNA. A,B: tunica albuginea. 1, 2, 5 and 10 μl of construct. In particular, FIGS. 16A-B show that the construct can induce a nearly 100% transfection of these cells in vitro, and that these cells become transformed into myofibroblasts, as evidenced by the expression of ASMA in the tunica albuginea by western blot (FIG. 16B). FIG. 16A shows the immunohistochemical localization of ASMA stained in dark gray in the tunical cells confirming the results obtained by western blot.

Figure 17A:
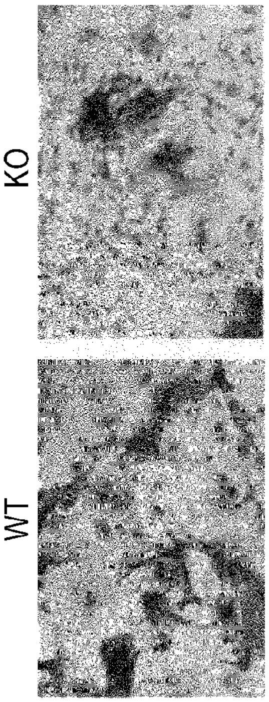
FIGS. 17A-B illustrate that pp 6 cells undergoing differentiation into myofibroblast and osteoblasts.
Figure 17B:
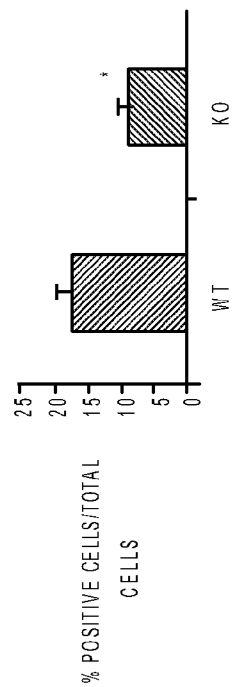

FIGS. 17A-B illustrate that pp 6 cells can undergo differentiation into myofibroblast and osteoblasts. In particular, FIGS. 17A-B illustrate that these effects of myostatin are not restricted to the penis. Instead, these effects can also occur in the skeletal muscle, as suggested by our experiments above in this tissue, as indicated by the comparison of ASMA expression in stem cells obtained from the mouse skeletal muscle. FIG. 17A shows the expression of ASMA (stained in dark gray) as a marker of myofibroblast conversion in pp 6 cells obtained from skeletal muscle of wild type and myostatin knock out mice. These cells can be converted in fibrotic myofibroblasts much more efficiently when they are derived from the wild type mouse (normal expression of myostatin) than when obtained from the myostatin knockout mouse (no myostatin expression). FIG. 17B shows the quantitative analysis of the number ASMA positive cell over the total number of cells per well.

In view of the foregoing, it is believed that blocking myostatin expression by shRNA or any other procedure, or inhibiting myostatin activity, may increase smooth muscle content in the penis and penile size, and counteract fibrosis, thus improving erectile function and counteracting impotence associated with penile fibrosis. In more general terms, the same process may counteract fibrosis in the skeletal muscle and other tissues.

In view of the foregoing, it is believed that inhibiting myostatin expression and/or activity, in addition to preventing skeletal muscle loss or inducing an increase in skeletal muscle mass, may be used therapeutically for: a) increasing penile smooth muscle content and size; b) increase smooth muscle content in other organs; and c) prevent fibrosis.

Exemplary penile conditions that can be treated by this approach may include, but are not limited to enlargement of penis size, or in the treatment or prevention of small penis size, cavernosal smooth muscle myopathies, congenital micropenis and other genetic abnormalities, effects of hypogonadism on penile size, penile trauma, hypospadias, transsexual penile construction, penile amputation, penile cancer, Peyronie's disease, vasculogenic erectile dysfunction related to penile fibrosis.

Exemplary fibrotic conditions in general that can be treated by this approach are: Peyronie's disease plaque, penile corporal fibrosis, penile veno-occlussive dysfunction, Dupuytren's disease nodules, vaginal fibrosis, clitoral fibrosis, female sexual arousal disorder, abnormal wound healing, keloid formation, general fibrosis of the kidney, bladder, prostate, skin, liver, lung, heart, intestines or any other localized or generalized fibrotic condition, vascular fibrosis, arterial intima hyperplasia, atherosclerosis, arteriosclerosis, restenosis, cardiac hypertrophy, hypertension or any condition characterized by excessive fibroblast cell proliferation or deposition of collagen and extracellular matrix in the blood vessels and/or heart, skeletal muscle atrophies and dystrophies in sarcopenia of old age, diabetes, kidney dialysis, prolonged immobilization, and related.

Based on the foregoing results, it is contemplated that the techniques described herein may be used, for example, to increase skeletal muscle mass, smooth muscle mass, increase penile size, decrease smooth muscle fibrosis and increase smooth muscle of the corpora cavernosa of the penis.

In the preceding detailed description, specific embodiments are described. It will, however, be evident that various modifications and changes may be made thereto without departing from the broader spirit and scope of the claims. The specification and drawings are, accordingly, to be regarded in an illustrative rather than restrictive sense.

What is claimed is:

1. A method for increasing smooth muscle mass comprising:

delivering a composition comprising an effective amount of a vector having a nucleotide sequence expressed as a shRNA having a property to inhibit myostatin expression to a penile smooth muscle tissue, wherein the shRNA is capable of inhibiting myostatin expression of a myostatin gene sequence comprising SEQ ID NO: 1 so as to increase the penile smooth muscle tissue mass; and applying an electrical pulse across a point of delivery to increase cellular uptake of the shRNA vector.

2. The method of claim 1, wherein the vector is one of a viral and a plasmid vector.

3. The method of claim 1, wherein delivering comprises locally introducing the vector including the nucleotide sequence to the mammalian tissue.

4. The method of claim 1, wherein delivering comprises in vivo injection of the vector including the nucleotide sequence to the mammalian tissue.

5. The method of claim 1, wherein delivering comprises a systemic delivery.

6. The method of claim 1, wherein the vector including the nucleotide sequence is present in an amount sufficient to measurably reduce fibrosis.

7. A method for increasing smooth muscle mass comprising:

inhibiting myostatin expression or activity by administering a treatment agent comprising a vector having a nucleotide sequence expressed as a shRNA having a property to inhibit myostatin expression to a penile smooth muscle tissue, wherein the vector including the nucleotide sequence is present in an amount sufficient to measureably increase penile smooth muscle mass, and wherein the shRNA is capable of inhibiting myostatin expression of a myostatin gene sequence comprising SEQ ID NO: 1; and applying an electrical pulse across a point of delivery to increase cellular uptake of the shRNA vector.

8. The method of claim 7, wherein increasing smooth muscle mass comprises increasing penis size.

9. The method of claim 7, wherein the vector including the nucleotide sequence is locally delivered to the smooth muscle mass.

10. The method of claim 4 wherein the vivo injection of the vector is performed repeatedly to maintain myostatin inhibition.

11. The method of claim 1 wherein the nucleotide sequence of the shRNA is represented by SEQ. ID NO.: 3.

12. A method for treating a penile condition comprising:

delivering a composition to a myostatin expressing penile tissue found in one of a corpora cavernosa or a tunica albuginea region of a penis, the composition comprising a vector having a nucleotide sequence expressed as a shRNA having a property to inhibit myostatin expression, wherein the vector including the nucleotide sequence is present in an amount sufficient to treat a penile condition.

13. The method of claim 12 wherein treating the penile condition comprises increasing a mass of the myostatin expressing penile tissue.

14. The method of claim 12 wherein treating the penile condition comprises counteracting fibrosis.

15. The method of claim 12 wherein the myostatin expressing tissue is a penile smooth muscle tissue found in the corpora cavernosa.

16. The method of claim 12 wherein the myostatin expressing tissue is a fibroblast or a myofibroblast found in the tunica albuginea.

* * * * *

UNITED STATES PATENT AND TRADEMARK OFFICE

CERTIFICATE OF CORRECTION

PATENT NO. : 8,426,374 B1
APPLICATION NO. : 11/744158
DATED : April 23, 2013
INVENTOR(S) : Magee et al.

It is certified that error appears in the above-identified patent and that said Letters Patent is hereby corrected as shown below:

In the Claims, Column 28, Claim 10, line 11, please delete “vivo” and insert --in vivo--.

Signed and Sealed this
Twenty-seventh Day of August, 2013

Teresa Stanek Rea
*Acting Director of the United States Patent and Trademark Office*